US006924266B2

(12) United States Patent
Averback

(10) Patent No.: US 6,924,266 B2
(45) Date of Patent: Aug. 2, 2005

(54) NTP-PEPTIDES AND METHOD FOR REMOVAL OF TUMORS

(75) Inventor: Paul Averback, Quebec (CA)

(73) Assignee: Nymox Corporation, St. Laurent (CA)

( * ) Notice: Subject to any disclaimer, the term of this patent is extended or adjusted under 35 U.S.C. 154(b) by 47 days.

(21) Appl. No.: 10/153,334

(22) Filed: May 24, 2002

(65) Prior Publication Data

US 2003/0096350 A1 May 22, 2003

Related U.S. Application Data

(60) Provisional application No. 60/293,156, filed on May 25, 2001.

(51) Int. Cl.[7] .......................... A61K 38/00; A61K 38/10; C07K 7/00; C07K 14/00
(52) U.S. Cl. ............................ 514/2; 530/300; 530/324; 530/325; 530/326; 530/327
(58) Field of Search ............................... 514/2; 530/300, 530/324, 325, 326, 327, 350, 387.1

(56) References Cited

U.S. PATENT DOCUMENTS

| | | | |
|---|---|---|---|
| 5,830,670 A | | 11/1998 | de la Monte et al. |
| 5,948,634 A | | 9/1999 | de la Monte et al. |
| 5,948,888 A | * | 9/1999 | de la Monte et al. ....... 530/350 |
| 6,071,705 A | | 6/2000 | Wands et al. |

FOREIGN PATENT DOCUMENTS

| | | |
|---|---|---|
| WO | WO 98 38204 A | 9/1998 |
| WO | WO 99/19347 | 4/1999 |
| WO | WO 00 34477 A | 6/2000 |
| WO | WO 00/58495 | 10/2000 |
| WO | WO 00/63230 | 10/2000 |
| WO | WO 02 34915 A | 5/2002 |
| WO | WO 02 074323 A | 9/2002 |
| WO | WO 02 092115 A | 11/2002 |

OTHER PUBLICATIONS

Wells (Sept. 18, 1990) "Additivity of Mutational Effects in Proteins." Biochemistry 29(37): 8509–8517.*
Ngo et al. (Mar. 2, 1995) "The Protein Folding Problem and Tertiary Structure Predication, Chapter 14: Computational Complexity Protein Structure Prediction, and the Levinthal Paradox" pp. 433–506.*

Bork (2000) "Powers and Pitfalls in Sequence Analysis: The 70% Hurdle." Genome Research 10:398–400.*
Skolnick and Fetrow (2000) "From gene to protein structure and function: novel applications of computational approaches in th genomic era." Trends in Biotech. 18(1): 34–39.*
Doerks et al., (Jun. 1998) "Protein annotation: detective work for function prediction." Trends in Genetics 14(6): 248–250.*
Smith and Zhang (Nov. 1997) "The challenges of genome sequence annotation or 'The devil is in the details'." Nature Biotechnology 15:1222–1223.*
Brenner (Apr. 1999) "Errors in genome annotation." Trends in Genetics 15(4): 132–133.*
Bork and Bairoch (Oct. 1996) "Go hunting in sequence databases but watch out for the traps." Trends in Genetics 12(10): 425–427.*
de la Monte et al. (Jun. 1996) "Modulation of neuronal thread protein expression with neuritic sprouting: relevance to Alzheimer's disease." Journal of the Neurological Sciences 138(1–2): 26–35.*
de la Monte et al.: "Characterization of the AD7C–NTP cDNA Expression in Alzheimer's Disease and Measurement of a 41–kD Protein in Cerebrospibal Fluid" Journal of Clincial Investigation, vol. 100, No. 12, Dec. 15, 1997, pp. 3093–3104.
International Search Report issued in PCT/CA02/00759, date of mailing Sep. 11, 2003.
Sijits, et al., *Immunodominant Mink Cell Focus–Inducing Murine Leukemia Virus (MuLV)–Encoded CTL Epitope, Identified by its MHC Class I–Binding Motif, Explains MuLV–Type Specificity of MCF–Directed Cytotoxic T Lymphocytes*, Journal of Immunology, The Williams Y Wilkins Co., Baltimore, vol. 152, 1994, pp. 106–116.

* cited by examiner

Primary Examiner—Sharon L. Turner
Assistant Examiner—Christopher James Nichols
(74) Attorney, Agent, or Firm—Hunton Williams LLP

(57) ABSTRACT

The present invention is directed to methods of treating conditions requiring removal or destruction of harmful or unwanted cells in a patient, such as benign and malignant tumors, using peptides derived from the amino acid sequences of neural thread proteins and related molecules.

7 Claims, 9 Drawing Sheets

Figure 1

AD7C-NTP [SEQ ID NO. 1]

```
   1  tttttttttttgag ATG GAG TTT TCG CTC TTG TTG CCC AGG CTG GAG TGC AAT GGC GCA ATC   62
   1                  M   E   F   S   L   L   L   P   R   L   E   C   N   G   A   I   16

63  TCA GCT CAC CGC AAC CTC CGC CTC CCG GGT TCA AGC GAT TCT CCT GCC TCA GCC TCC CCA  122
  17   S   A   H   R   N   L   R   L   P   G   S   S   D   S   P   A   S   A   S   P   36

123  GTA GCT GGG ATT ACA GGC ATG TGC ACC CAC GCT CGG CTA ATT TTG TAT TTT TTT TTA GTA  182
  37   V   A   G   I   T   G   M   C   T   H   A   R   L   I   L   Y   F   F   L   V   56

183  GAG ATG GAG TTT CTC CAT GTT GGT CAG GCT GGT CTC GAA CTC CCG ACC TCA GAT GAT CCC  242
  57   E   M   E   F   L   H   V   G   Q   A   G   L   E   L   P   T   S   D   D   P   76

243  TCC GTC TCG GCC TCC CAA AGT GCT AGA TAC AGG ACT GGC CAC CAT GCC CGG CTC TGC CTG  302
  77   S   V   S   A   S   Q   S   A   R   Y   R   T   G   H   H   A   R   L   C   L   96

303  GCT AAT TTT TGT GGT AGA AAC AGG GTT TCA CTG ATG TGC CCA AGC TGG TCT CCT GAG CTC  362
  97   A   N   F   C   G   R   N   R   V   S   L   M   C   P   S   W   S   P   E   L  116

363  AAG CAG TCC ACC TGC CTC AGC CTC CCA AAG TGC TGG GAT TAC AGG CGT GCA GCC GTG CCT  422
 117   K   Q   S   T   C   L   S   L   P   K   C   W   D   Y   R   R   A   A   V   P  136

423  GGC CTT TTT ATT TTA TTT TTT TTA AGA CAC AGG TGT CCC ACT CTT ACC CAG GAT GAA GTG  482
 137   G   L   F   I   L   F   F   L   R   H   R   C   P   T   L   T   Q   D   E   V  156

483  CAG TGG TGT GAT CAC AGC TCA CTG CAG CCT TCA ACT CCT GAG ATC AAG CAT CCT CCT GCC  542
 157   Q   W   C   D   H   S   S   L   Q   P   S   T   P   E   I   K   H   P   P   A  176

543  TCA GCC TCC CAA GTA GCT GGG ACC AAA GAC ATG CAC CAC TAC ACC TGG CTA ATT TTT ATT  602
 177   S   A   S   Q   V   A   G   T   K   D   M   H   H   Y   T   W   L   I   F   I  196

603  TTT ATT TTT AAT TTT TTG AGA CAG AGT CTC AAC TCT GTC ACC CAG GCT GGA GTG CAG TGG  662
 197   F   I   F   N   F   L   R   Q   S   L   N   S   V   T   Q   A   G   V   Q   W  216

663  CGC AAT CTT GGC TCA CTG CAA CCT CTG CCT CCC GGG TTC AAG TTA TTC TCC TGC CCC AGC  722
 217   R   N   L   G   S   L   Q   P   L   P   P   G   F   K   L   F   S   C   P   S  236

723  CTC CTG AGT AGC TGG GAC TAC AGG CGC CCA CCA CGC CTA GCT AAT TTT TTT GTA TTT TTA  782
 237   L   L   S   S   W   D   Y   R   R   P   P   R   L   A   N   F   F   V   F   L  256

783  GTA GAG ATG GGG TTC ACC ATG TTC GCC AGG TTG ATC TTG ATC TCT GGA CCT TGT GAT CTG  842
 257   V   E   M   G   F   T   M   F   A   R   L   I   L   I   S   G   P   C   D   L  276

843  CCT GCC TCG GCC TCC CAA AGT GCT GGG ATT ACA GGC GTG AGC CAC CAC GCC CGG CTT ATT  902
 277   P   A   S   A   S   Q   S   A   G   I   T   G   V   S   H   H   A   R   L   I  296

903  TTT AAT TTT TGT TTG TTT GAA ATG GAA TCT CAC TCT GTT ACC CAG GCT GGA GTG CAA TGG  962
 297   F   N   F   C   L   F   E   M   E   S   H   S   V   T   Q   A   G   V   Q   W  316

963  CCA AAT CTC GGC TCA CTG CAA CCT CTG CCT CCC GGG CTC AAG CGA TTC TCC TGT CTC AGC 1022
 317   P   N   L   G   S   L   Q   P   L   P   P   G   L   K   R   F   S   C   L   S  336

1023  CTC CCA AGC AGC TGG GAT TAC GGG CAC CTG CCA CCA CAC CCC GCT AAT TTT TGT ATT TTC 1082
 337   L   P   S   S   W   D   Y   G   H   L   P   P   H   P   A   N   F   C   I   F  356

1083  ATT AGA GGC GGG GTT TCA CCA TAT TTG TCA GGC TGG TCT CAA ACT CCT GAC CTC AGG tgac 1143
 357   I   R   G   G   V   S   P   Y   L   S   G   W   S   Q   T   P   D   L   R      375

1144  ccaccrgcctcagcctrccaaagtgctgggattacaggcgtgagccacctcacccagccggctaatttagataaaaaat 1223

1224  atgtagcaatgggggtcttgctatgttgcccaggctggtctcaaacttctggcttcatgcaatccttccaaatgagcca 1303

1304  caacacccagccagtcacattttttaaacagttacatctttattttagtatactagaaagtaatacaataaacatgtcaa 1383

1384  acctgcaaattcagtagtaacagagttctttttataacttttaaacaaagctttagagca                    1442
```

Figure 2

NTP[122] [SEQ ID NO. 2]

```
1    Met-Met-Val-Cys-Trp-Asn-Arg-Phe-Gly-Lys-
      M   M   V   C   W   N   R   F   G   K

11   Trp-Val-Tyr-Phe-Ile-Ser-Ala-Ile-Phe-Asn-
      W   V   Y   F   I   S   A   I   F   N

21   Phe-Gly-Pro-Arg-Tyr-Leu-Tyr-His-Gly-Val-
      F   G   P   R   Y   L   Y   H   G   V

31   Pro-Phe-Tyr-Phe-Leu-Ile-Leu-Val-Arg-Ile-
      P   F   Y   F   L   I   L   V   R   I

41   Ile-Ser-Phe-Leu-Ile-Gly-Asp-Met-Glu-Asp-
      I   S   F   L   I   G   D   M   E   D

51   Val-Leu-Leu-Asn-Cys-Thr-Leu-Leu-Lys-Arg-
      V   L   L   N   C   T   L   L   K   R

61   Ser-Ser-Arg-Phe-Arg-Phe-Trp-Gly-Ala-Leu-
      S   S   R   F   R   F   W   G   A   L

71   Val-Cys-Ser-Met-Asp-Ser-Cys-Arg-Phe-Ser
      V   C   S   M   D   S   C   R   F   S

81   Arg-Val-Ala-Val-Thr-Tyr-Arg-Phe-Ile-Thr-
      R   V   A   V   T   Y   R   F   I   T

91   Leu-Leu-Asn-Ile-Pro-Ser-Pro-Ala-Val-Trp-
      L   L   N   I   P   S   P   A   V   W

101  Met-Ala-Arg-Asn-Thr-Ile-Asp-Gln-Gln-Val-
      M   A   R   N   T   I   D   Q   Q   V

111  Leu-Ser-Arg-Ile-Lys-Leu-Glu-Ile-Lys-Arg-
      L   S   R   I   K   L   E   I   K   R

121  Cys-Leu
      C   L
```

Figure 3

NTP[112] [SEQ ID NO. 3]

| | | | | | | | | | | |
|---|---|---|---|---|---|---|---|---|---|---|
| 1 | Met-Ala-Gln-Ser-Arg-Leu-Thr-Ala-The-Ser- | | | | | | | | | |
| | M | A | Q | S | R | L | T | A | T | S |
| 11 | Ala-Ser-Arg-Val-Gln-Ala-Ile-Leu-Leu-Ser- | | | | | | | | | |
| | A | S | R | V | Q | A | I | L | L | S |
| 21 | Gln-Pro-Pro-Lys-Gln-Leu-Gly-Leu-Arg-Ala- | | | | | | | | | |
| | Q | P | P | K | Q | L | G | L | R | A |
| 31 | Pro-Ala-Asn-Thr-Pro-Leu-Ile-Phe-Val-Phe- | | | | | | | | | |
| | P | A | N | T | P | L | I | F | V | F |
| 41 | Ser-Leu-Glu-Ala-Gly-Phe-His-His-Ile-Cys- | | | | | | | | | |
| | S | L | E | A | G | F | H | H | I | C |
| 51 | Gln-Ala-Gly-Leu-Lys-Leu-Leu-Thr-Ser-Gly- | | | | | | | | | |
| | Q | A | G | L | K | L | L | T | S | G |
| 61 | Asp-Pro-Pro-Ala-Ser-Ala-Phe-Gln-Ser-Ala- | | | | | | | | | |
| | D | P | P | A | S | A | F | Q | S | A |
| 71 | Gly-Ile-Thr-Gly-Val-Ser-His-Leu-Thr-Gln- | | | | | | | | | |
| | G | I | T | G | V | S | H | L | T | Q |
| 81 | Pro-Ala-Asn-Leu-Asp-Lys-Lys-Ile-Cys-Ser- | | | | | | | | | |
| | P | A | N | L | D | K | K | I | C | S |
| 91 | Asn-Gly-Gly-Ser-Cys-Tyr-Val-Ala-Gln-Ala- | | | | | | | | | |
| | N | G | G | S | C | Y | V | A | Q | A |
| 101 | Gly-Leu-Lys-Leu-Leu-Ala-Ser-Cys-Asn-Pro- | | | | | | | | | |
| | G | L | K | L | L | A | S | C | N | P |
| 111 | Ser-Lys | | | | | | | | | |
| | S | K | | | | | | | | |

Figure 4

NTP[106] [SEQ ID NO. 4]

| | | | | | | | | | | |
|---|---|---|---|---|---|---|---|---|---|---|
| 1 | Met- | Trp- | Thr- | Leu- | Lys- | Ser- | Ser- | Leu- | Val- | Leu- |
| | M | W | T | L | K | S | S | L | V | L |
| 11 | Leu- | Leu- | Cys- | Leu- | Thr- | Cys- | Ser- | Tyr- | Ala- | Phe- |
| | L | L | C | L | T | C | S | Y | A | F |
| 21 | Met- | Phe- | Ser- | Ser- | Leu- | Arg- | Gln- | Lys- | Thr- | Ser- |
| | M | F | S | S | L | R | Q | K | T | S |
| 31 | Glu- | Pro- | Gln- | Gly- | Lys- | Val- | Pro- | Cys- | Gly- | Glu- |
| | E | P | Q | G | K | V | P | C | G | E |
| 41 | His- | Phe- | Arg- | Ile- | Arg- | Gln- | Asn- | Leu- | Pro- | Glu- |
| | H | F | R | I | R | Q | N | L | P | E |
| 51 | His- | Thr- | Gln- | Gly- | Trp- | Leu- | Gly- | Ser- | Lys- | Trp- |
| | H | T | Q | G | W | L | G | S | K | W |
| 61 | Leu- | Trp- | Leu- | Leu- | Phe- | Ala- | Val- | Val- | Pro- | Phe- |
| | L | W | L | L | F | A | V | V | P | F |
| 71 | Val- | Ile- | Leu- | Lys- | Cys- | Gln- | Arg- | Asp- | Ser- | Glu- |
| | V | I | L | K | C | Q | R | D | S | E |
| 81 | Lys- | Asn- | Lys- | Val- | Arg- | Met- | Ala- | Pro- | Phe- | Phe- |
| | K | N | K | V | R | M | A | P | F | F |
| 91 | Leu- | His- | His- | Ile- | Asp- | Ser- | Ile- | Ser- | Gly- | Val- |
| | L | H | H | I | D | S | I | S | G | V |
| 101 | Ser- | Gly- | Lys- | Arg- | Met- | Phe | | | | |
| | S | G | K | R | M | F | | | | |

Figure 5

NTP [106] [SEQ ID NO. 5]

| | | | | | | | | | | |
|---|---|---|---|---|---|---|---|---|---|---|
| 1 | Met- | Phe- | Phe- | Val- | Leu- | Tyr- | Arg- | Phe- | Cys- | Phe- |
| | M | F | F | V | L | Y | R | F | C | F |
| 11 | Cys- | Phe- | Phe- | Glu- | Thr- | Glu- | Ser- | His- | Ser- | Leu- |
| | C | F | F | E | T | E | S | H | S | L |
| 21 | Thr- | Gln- | Ala- | Gly- | Val- | Gln- | Trp- | Cys- | Glu- | Leu- |
| | T | Q | A | G | V | Q | W | C | E | L |
| 31 | Gly- | Ser- | Pro- | Gln- | Pro- | Leu- | Pro- | Ser- | Gly- | Phe- |
| | G | S | P | Q | P | L | P | S | G | F |
| 41 | Lys- | Arg- | Phe- | Ser- | Cys- | Leu- | Ser- | Leu- | Leu- | Ser- |
| | K | R | F | S | C | L | S | L | L | S |
| 51 | Ser- | Trp- | Asp- | Tyr- | Ser- | His- | Glu- | Pro- | Pro- | His- |
| | S | W | D | Y | S | H | E | P | P | H |
| 61 | Pro- | Val- | Ile- | Cys- | Ser- | Phe- | Leu- | Met- | Glu- | Lys- |
| | P | V | I | C | S | F | L | M | E | K |
| 71 | Cys- | Leu- | Ile- | Leu- | Tyr- | Lys- | Pro- | Asn- | Gly- | Asp- |
| | C | L | I | L | Y | K | P | N | G | D |
| 81 | Thr- | Ile- | Gly- | Pro- | Ile- | Leu- | Val- | Gln- | Gln- | Gly- |
| | T | I | G | P | I | L | V | Q | Q | G |
| 91 | Lys- | Arg- | Gln- | Lys- | Leu- | Tyr- | Ile- | Ser- | Ala- | Asp- |
| | K | R | Q | K | L | Y | I | S | A | D |
| 100 | Leu- | Val- | His- | Leu- | Ile- | Ala | | | | |
| | L | V | H | L | I | A | | | | |

Figure 6

NTP[98] [SEQ ID NO. 6]

| | |
|---|---|
| 1 | Glu-Ala-Tyr-Tyr-Thr-Met-Leu-His-Leu-Pro- <br> E   A   Y   Y   T   M   L   H   L   P |
| 11 | Thr-Thr-Asn-Arg-Pro-Lys-Ile-Ala-His-Cys <br> T   T   N   R   P   K   I   A   H   C |
| 21 | Ile-Leu-Phe-Asn-Gln-Pro-His-Ser-Pro-Arg- <br> I   L   F   N   Q   P   H   S   P   R |
| 31 | Ser-Asn-Ser-His-Ser-His-Pro-Asn-Pro-Leu- <br> S   N   S   H   S   H   P   N   P   L |
| 41 | Lys-Leu-His-Arg-Arg-Ser-His-Ser-His-Asn- <br> K   L   H   R   R   S   H   S   H   N |
| 51 | Arg-Pro-Arg-Ala-Tyr-Ile-Leu-Ile-Thr-Ile- <br> R   P   R   A   Y   I   L   I   T   I |
| 61 | Leu-Pro-Ser-Lys-Leu-Lys-Leu-Arg-Thr-His- <br> L   P   S   K   L   K   L   R   T   H |
| 71 | Ser-Gln-Ser-His-His-Asn-Pro-Leu-Ser-Arg- <br> S   Q   S   H   H   N   P   L   S   R |
| 81 | Thr-Ser-Asn-Ser-Thr-Pro-Thr-Asn-Ser-Phe- <br> T   S   N   S   T   P   T   N   S   F |
| 91 | Leu-Met-Thr-Ser-Ser-Lys-Pro-Arg <br> L   M   T   S   S   K   P   R |

Figure 7

NTP[75] [SEQ ID NO. 7]

| | | | | | | | | | | |
|---|---|---|---|---|---|---|---|---|---|---|
| 1 | Ser- | Ser- | Ser- | Leu- | Gly- | Leu- | Pro- | Lys- | Cys- | Trp- |
| | S | S | S | L | G | L | P | K | C | W |
| 11 | Asp- | Tyr- | Arg- | His- | Glu- | Leu- | Leu- | Ser- | Leu- | Ala- |
| | D | Y | R | H | E | L | L | S | L | A |
| 21 | Leu- | Met- | Ile- | Asn- | Phe- | Arg- | Val- | Met- | Ala- | Cys- |
| | L | M | I | N | F | R | V | M | A | C |
| 31 | Thr- | Phe- | Lys- | Gln- | His- | Ile- | Glu- | Leu- | Arg- | Gln- |
| | T | F | K | Q | H | I | E | L | R | Q |
| 41 | Lys- | Ile- | Ser- | Ile- | Val- | Pro- | Arg- | Lys- | Leu- | Cys- |
| | K | I | S | I | V | P | R | K | L | C |
| 51 | Cys- | Met- | Gly- | Pro- | Val- | Cys- | Pro- | Val- | Lys- | Ile- |
| | C | M | G | P | V | C | P | V | K | I |
| 61 | Ala- | Leu- | Leu- | Thr- | Ile- | Asn- | Gly- | His- | Cys- | Thr- |
| | A | L | L | T | I | N | G | H | C | T |
| 71 | Trp- | Leu- | Pro- | Ala- | Ser | | | | | |
| | W | L | P | A | S | | | | | |

Figure 8

NTP[68] [SEQ ID NO. 8]

```
1    Met-Phe-Val-Phe-Cys-Leu-Ile-Leu-Asn-Arg-
     M   F   V   F   C   L   I   L   N   R

11   Glu-Lys-Ile-Lys-Gly-Gly-Asn-Ser-Ser-Phe-
     E   K   I   K   G   G   N   S   S   F

21   Phe-Leu-Leu-Ser-Phe-Phe-Phe-Ser-Phe-Gln-
     F   L   L   S   F   F   F   S   F   Q

31   Asn-Cys-Cys-Gln-Cys-Phe-Gln-Cys-Arg-Thr-
     N   C   C   Q   C   F   Q   C   R   T

41   Thr-Glu-Gly-Tyr-Ala-Val-Glu-Cys-Phe-Tyr-
     T   E   G   Y   A   V   E   C   F   Y

51   Cys-Leu-Val-Asp-Lys-Ala-Ala-Phe-Glu-Cys-
     C   L   V   D   K   A   A   F   E   C

61   Trp-Trp-Phe-Tyr-Ser-Phe-Asp-Thr
     W   W   F   Y   S   F   D   T
```

Figure 9

NTP[61] [SEQ ID NO. 9]

```
1    Met-Glu-Pro-His-Thr-Val-Ala-Gln-Ala-Gly-
     M   E   P   H   T   V   A   Q   A   G

11   Val-Pro-Gln-His-Asp-Leu-Gly-Ser-Leu-Gln-
     V   P   Q   H   D   L   G   S   L   Q

21   Ser-Leu-Leu-Pro-Arg-Phe-Lys-Arg-Phe-Ser-
     S   L   L   P   R   F   K   R   F   S

31   Cys-Leu-Ile-Leu-Pro-Lys-Ile-Trp-Asp-Tyr-
     C   L   I   L   P   K   I   W   D   Y

41   Arg-Asn-Met-Asn-Thr-Ala-Leu-Ile-Lys-Arg-
     R   N   M   N   T   A   L   I   K   R

51   Asn-Arg-Tyr-Thr-Pro-Glu-Thr-Gly-Arg-Lys-
     N   R   Y   T   P   E   T   G   R   K

61   Ser
     S
```

NTP-PEPTIDES AND METHOD FOR REMOVAL OF TUMORS

This application claims priority to U.S. Provisional Patent Application No. 60/293,156, entitled: "Peptides Effective in the Treatment of Tumors and Other conditions Requiring the Removal or Destruction of Cells," and filed on May 25, 2001, the disclosure of which is incorporated by reference herein in its entirety.

BACKGROUND OF THE INVENTION

1. Field of the Invention

The present invention is directed to methods of treating conditions requiring removal or destruction of cellular elements, such as benign or malignant tumors in humans, using peptides containing amino acid sequences corresponding to part of the amino acid sequence of neural thread proteins. The method includes, but is not limited to, administering the compounds intramuscularly, orally, intravenously, intrathecally, intratumorally, intranasally, topically, transdermally, etc., either alone or conjugated to a carrier.

2. Description of Related Art

Many medical treatments and procedures involve the removal or destruction of harmful or unwanted tissue. Examples of such important treatments include the surgical removal of cancerous growths, the destruction of metatastic tumors through chemotherapy, and the reduction of glandular (e.g. prostate) hyperplasia. Other examples include the removal of unwanted facial hair, the removal of warts, and the removal of unwanted fatty tissue. Many of these treatments are either invasive through complicated and dangerous surgery, or destroy un-targeted otherwise healthy tissue through non-invasive techniques.

There is a need for an effective agent that will destroy and either: (i) facilitate without surgery the removal of; or (ii) inhibit the further growth of harmful or unwanted cells and tissue, but will have mainly local effects and minimal or no systemic toxicity.

Neural thread proteins and their related molecules are one class of such agents as disclosed in pending U.S. patent application Ser. No. 10/092,934, Methods of Treating Tumors and Related Conditions Using Neural Thread Proteins, the disclosure of which is incorporated be reference herein in its entirety.

Cancer is an abnormality in a cell's internal regulatory mechanisms that results in uncontrolled growth and reproduction of the cell. Normal cells make up tissues, and when these cells lose their ability to behave as a specified, controlled, and coordinated unit, (dedifferentiation) the defect leads to disarray amongst the cell population. When this occurs, a tumor is formed.

Benign overgrowths of tissue are abnormalities in which it is desirable to remove cells from an organism. Benign tumors are cellular proliferations that do not metastasize throughout the body but do, however, cause disease symptoms. Such tumors can be lethal if they are located in inaccessible areas in organs such as the brain. Benign tumors exist in many other organs including lung, skin, pituitary, thyroid, adrenal cortex and medulla, ovary, uterus, testis, connective tissue, muscle, intestines, ear, nose, throat, tonsils, mouth, liver, gall bladder, pancreas, prostate, heart, and other organs.

Surgery often is the first step in the treatment of cancer. The objective of surgery varies. Sometimes it is used to remove as much of the evident tumor as possible, or at least to "debulk" it (remove the major bulk(s) of tumor so that there is less that needs to be treated by other means). Depending on the cancer type and location, surgery also may provide some symptomatic relief to the patient. For instance, if a surgeon can remove a large portion of an expanding brain tumor, the pressure inside the skull will decrease, leading to improvement in the patient's symptoms.

Not all tumors are amenable to surgery. Some may be located in parts of the body that make them impossible to completely remove. Examples of these would be tumors in the brainstem (a part of the brain that controls breathing) or a tumor which has grown in and around a major blood vessel. In these cases, the role of surgery is limited due to the high risk associated with tumor removal.

In some cases, surgery is not used to debulk tumor because it is simply not necessary. An example is Hodgkin's lymphoma, a cancer of the lymph nodes that responds very well to combinations of chemotherapy and radiation therapy. In Hodgkin's lymphoma, surgery is rarely needed to achieve cure, but almost always used to establish a diagnosis.

Chemotherapy is another common form of cancer treatment. Essentially, it involves the use of medications (usually given by mouth or injection) which specifically attack rapidly dividing cells (such as those found in a tumor) throughout the body. This makes chemotherapy useful in treating cancers that have already metastasized, as well as tumors that have a high chance of spreading through the blood and lymphatic systems but are not evident beyond the primary tumor. Chemotherapy also may be used to enhance the response of localized tumors to surgery and radiation therapy. This is the case, for example, for some cancers of the head and neck.

Unfortunately, other cells in the human body that normally divide rapidly (such as the lining of the stomach and hair) also may be affected by chemotherapy. For this reason, some (though not all) chemotherapy agents induce nausea or hair loss. These side effects are temporary, and doctors have medications they can provide to help alleviate many of these side effects. So, in general, chemotherapy treatments are well tolerated by patients. As our knowledge has continued to grow, researchers have devised newer chemotherapeutic agents that are not only better at killing cancer cells, but that also have fewer side effects for the patient.

Chemotherapy is administered to patients in a variety of ways. Some are pills that are taken daily or once a week or some other schedule and some are administered by an intravenous injection. For injectable chemotherapy, a patient goes to the doctor's office or hospital for treatment. Other chemotherapeutic agents require continuous infusion into the bloodstream, 24 hours a day. For these types of chemotherapy, a minor surgical procedure is performed to implant a small pump worn by the patient. The pump then slowly administers the medication. In many cases, a permanent port is placed in a patient's vein to eliminate the requirement of repeated needle sticks.

Radiation therapy is another commonly used weapon in the fight against cancer. Radiation kills cancer by damaging the DNA within the tumor cells. The radiation is "applied" two possible ways. The first, and most common, involves pointing a beam of radiation at the patient in a highly precise manner, focusing on the tumor. To do this, a patient lies on a table and the beam moves around him/her. This only takes a couple of minutes, but is done five days per week for 3–6 weeks (depending on the type of tumor), to achieve a particular total prescribed "dose."

Another radiation method sometimes employed, called brachytherapy, involves taking radioactive pellets ("seeds") or wires and implanting them in the body in the area of the tumor. The implants can be temporary or permanent. For permanent implants, the radiation in the seeds "decays" or fades away over a period of days or weeks so that the patient is not radioactive. For temporary implants, the entire dose of radiation usually is delivered in about two days, and the patient must remain in the hospital during that time. For both types of brachytherapy, radiation generally is delivered to a very targeted area to gain local control over a cancer (as opposed to treating the whole body, as chemotherapy does.)

Some highly selected patients may be referred for bone marrow transplants. This procedure is usually performed either because a patient has a cancer that is particularly aggressive or because they have a cancer that has relapsed after being treated with conventional therapy. Bone marrow transplantation is a complicated procedure. There are many types, and they vary in their potential for causing side effects and cure. Most transplants are performed at special centers, and in many cases their use is considered investigational.

Additional therapies exist, although most of them are still being explored in clinical trials and have not yet become standard care. Examples include the use of immunotherapy, monoclonal antibodies, anti-angiogenesis factors, and gene therapy.

Immunotherapy: Various techniques have been designed to help the patient's own immune system fight the cancer, quite separately from radiation or chemotherapy. Oftentimes, to achieve the goal researchers inject the patient with a specially derived vaccine. Most research in this area has been conducted on melanoma, though other cancers are also now being targeted.

Monoclonal Antibodies: These are small proteins that are especially designed to attach to cancerous cells (and not normal cells) by taking advantage of differences between cancerous and non-cancerous cells in their cell membranes. Before administering the antibodies to the patient, they often are "tagged" (attached) to various cytotoxic compounds or are made radioactive, such that the antibody preferentially targets the cancerous cells, thereby delivering the toxic agent to the desired cells.

Anti-Angiogenesis Factors: As cancer cells rapidly divide and tumors grow, they can soon outgrow their blood supply. To compensate for this, some tumors secrete a compound which has been shown to help induce the growth of blood vessels in their vicinity, thus assuring the cancer cells a continuous supply of nutrients. Recently, researchers have been studying ways to turn this process off by stopping the growth of blood vessels and/or by preventing additional blood from reaching the cancer cells.

Gene Therapy: Cancer is the product of a series of mutations that ultimately lead to the production of a cancer cell and its excessive proliferation. Cancers can be treated by introducing genes to the cancer cells that will act either to check or stop the cancer's proliferation, turn on the cell's programmed cell mechanisms to destroy the cell, enhance immune recognition of the cell, or express a pro-drug that converts to a toxic metabolite or a cytokine that inhibits tumor growth.

Benign tumors and malformations also can be treated by a variety of methods including surgery, radiotherapy, drug therapy, thermal or electric ablation, cryotherapy, and others. Although benign tumors do not metastasize, they can grow large and they can recur. Surgical extirpation of benign tumors has all the difficulties and side effects of surgery in general and oftentimes must be repeatedly performed for some benign tumors, such as for pituitary adenomas, meningeomas of the brain, prostatic hyperplasia, and others.

Other conditions involving unwanted cellular elements where selective cellular removal is desirable include, for example, heart disease and strokes. These conditions typically are caused by atherosclerosis, a proliferative lesion of fibrofatty and modified smooth muscle elements that distorts the blood vessel wall, narrow the lumen, constrict blood flow, predispose to focal blood clots, and ultimately lead to blockage and infarction. Treatments for atherosclerosis include bypass grafts; artificial grafts; angioplasty with recanalization, curettage, radiation, laser, or other removal; pharmacotherapy to inhibit atherosclerosis through lipid reduction; anti-clotting therapies; and general measures of diet, exercise, and lifestyle. A method for removing atherosclerotic lesions without the risk and side effects of surgical procedures is needed.

Other examples of unwanted cellular elements where selective cellular removal is desirable include viral induced growths, such as warts. Another example is hypertrophic inflammatory masses found in inflammatory conditions, and hypertrophic scars or keloids. Still other examples are found in cosmetic contexts such as the removal of unwanted hair, e.g., facial hair, or for shrinkage of unwanted tissue areas for cosmetic purposes, such as in the facial dermis and connective tissues or in the dermas and connective tissue of the extremities.

Still other examples will be readily apparent to those of ordinary skill in the art. In all or most of these examples there is a need for treatments that can remove or destroy the unwanted cellular elements without the risks and side effects of conventional therapies. A need also exists to remove the unwanted cellular elements with more precision.

Neural thread proteins (NTP) are a family of recently characterized brain proteins. One member of this family, AD7C-NTP, is a ~41 kD membrane associated phosphoprotein with functions associated with neuritic sprouting (de la Monte et al., *J. Clin. Invest.*, 100:3093–3104 (1997); de la Monte et al., *Alz. Rep.*, 2:327–332 (1999); de la Monte S M and Wands J R, *Journal of Alzheimer's Disease*, 3:345–353 (2001)). The gene that encodes AD7C-NTP and predicted protein sequence for AD7C-NTP has been identified and described (de la Monte et al., *J. Clin. Invest.*, 100:3093–3104 (1997)). In addition to the ~41 kD species, other species of neural thread protein (~26 kD, ~21 kD, ~17 kD, and ~15 kD) have been identified and associated with neuroectodermal tumors, astrocytomas, and glioblastomas and with injury due to hypoxia, schema, or cerebral infarction (Xu et al., *Cancer Research*, 53:3823–3829 (1993); de la Monte et al., *J. Neuropathol. Exp. Neurol.*, 55(10):1038–50 (1996), de la Monte et al., *J. Neurol. Sci.*, 138(1–2):26–35 (1996); de la Monte et al., *J. Neurol. Sci.*, 135(2):118–25 (1996); de la Monte et al., *J. Clin. Invest.*, 100:3093–3104 (1997); and de la Monte et al., *Alz. Rep.*, 2:327–332 (1999)).

Species of neural thread protein have been described and claimed in U.S. Pat. Nos. 5,948,634; 5,948,888; and 5,830,670, all for "Neural Thread Protein Gene Expression and Detection of Alzheimer's Disease" and in U.S. Pat. No. 6,071,705 for "Method of Detecting Neurological Disease or Dysfunction." The disclosures of these patents are specifically incorporated herein by reference in their entirety. As described therein, NTP is upregulated and produced during cell death. Thus, dead and dying nerve cells are described as overproducing NTP, and accordingly, its presence indicates the death of nerve cells and the onset of Alzheimer's disease (AD).

Other species of neural thread protein have been identified as other products of the AD7C-NTP gene (e.g. a 112 amino acid protein described in NCBI Entrez-Protein database Accession #XP_032307 PID g15928971) or as being similar to neural thread proteins (e.g. a 106 amino acid protein described in NCBI Entrez-Protein database Accession #AAH14951 PID g15928971, another 106 amino acid protein described in NCBI Entrez-Protein database Accession #XP_039102 PID g18599339 and a 61 amino acid protein described in NCBI Entrez-Protein database Accession #AAH02534 PID g12803421).

Neural thread protein is associated with AD and NTP is upregulated in association with cell death in AD. AD7C-NTP mRNA is upregulated in AD brain compared to controls; AD7C-NTP protein levels in brain and in CSF are higher in AD than controls; and AD7C-NTP immunoreactivity is found in senile plaques, in neurofibrillary tangles (NFT), in degenerating neurons, neuropil threads, and dystrophic neurotic sprouts in AD and Down syndrome brains (Ozturk et al., *Proc. Natl. Acad. Sci. USA*, 86:419–423 (1989); de la Monte et al., *J. Clin. Invest.*, 86(3):1004–13 (1990); de la Monte et al., *J. Neurol. Sci.*, 113(2):152–64 (1992); de la Monte et al., *Ann. Neurol.*, 32(6):733–42 (1992); de la Monte et al., *J. Neuropathol. Exp. Neurol.*, 55(10):1038–50 (1996), de la Monte et al., *J. Neurol. Sci.*, 138(1–2):26–35 (1996); de la Monte et al., *J. Neurol. Sci.*, 135(2):118–25 (1996); de la Monte et al., *J. Clin. Invest.*, 100:3093–3104 (1997); and de la Monte et al., *Alz. Rep.*, 2:327–332 (1999)). NTP is localized within cells, within fine processes within the neuropil, or is extracellular in both AD and Down's Syndrome brains. de la Monte et al., *Ann. Neurol.*, 32(6):733–42 (1992).

Elevated levels of AD7C-NTP protein have been found in both CSF and urine of AD patients (de la Monte and Wands, *Front Biosci* 7: 989–96 (2002); de la Monte and Wands, *Journal of Alzheimer's Disease* 3: 345–353 (2001); Munzar et al, *Alzheimer's Reports* 4: 61–65 (2001); Kahle et al, *Neurology* 54: 1498–1504 (2000) and Averback *Neurology* 55: 1068 (2000); Munzar et al, *Alzheimer Reports* 3: 155–159 (2000); de la Monte et al, *Alzheimer's Reports* 2: 327–332 (1999); Ghanbari et al, *J Clin Lab Anal* 12: 285–288 (1998); Ghanbari et al, *J Clin Lab Anal* 12: 223–226 (1998); Ghanbari et al, *Journal of Contemporary Neurology* 1998; 4A: 2–6 (1998); and de la Monte et al, *J Clin Invest* 100: 3093–3104 (1997).

Over-expression of NTP also has been linked to the process of cell death in Alzheimer's disease (de la Monte and Wands, *J. Neuropatho. and Exp. Neuro.*, 60:195–207 (2001); de la Monte and Wands, *Cell Mol Life Sci* 58: 844–49 (2001). AD7C-NTP has also been identified in Down's Syndrome brain tissue (Wands et al., International Patent Publication No. WO 90/06993; de la Monte et al, *J Neurol Sci* 135: 118–25 (1996); de la Monte et al., *Alz. Rep.*, 2:327–332 (1999)). Some evidence suggests that over-expression of NTP also may be associated with normal tension glaucoma (Golubnitschaja-Labudova et al, *Curr Eye Res* 21: 867–76 (2000)).

NTP has proven to be an effective agent for causing cell death both in vitro in glioma and neuroblastoma cell cultures and in vivo in normal rodent muscle tissue, subcutaneous connective tissue, and dermis, and in a variety of different human and non-human origin tumors, including mammary carcinoma, skin carcinoma and papilloma, colon carcinoma, glioma of brain, and others in rodent models. See the pending U.S. patent application Ser. No. 10/092,934, Methods of Treating Tumors and Related Conditions Using Neural Thread Proteins, the disclosure of which is incorporated by reference herein in its entirety.

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to the present invention.

SUMMARY OF THE INVENTION

There remains a need in the art for new, less toxic treatments for treating unwanted cellular elements. This invention relates to the surprising discovery that peptides containing amino acid sequences corresponding to part of the amino acid sequence of neural thread proteins are also such agents.

The present invention relates to methods of treating unwanted cellular proliferations, such as benign and malignant tumors, glandular (e.g. prostate) hyperplasia, unwanted facial hair, warts, and unwanted fatty tissue. Such a method comprises administering to a mammal in need a therapeutically effective amount of a peptide comprising amino acid sequences corresponding to part of the amino acid sequence of neural thread protein (NTP).

Such a peptide ("NTP peptide") can be administered alone or conjugated to a carrier or an antibody. The NTP peptide can be administered intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc., either alone or conjugated to a carrier. Alternatively, the NTP peptide can be expressed in vivo by administering a gene that expresses the peptide, by administering a vaccine that induces such production or by introducing cells, bacteria or viruses that express the peptide in vivo, either because of genetic modification or otherwise. In addition, the NTP peptide may be used in conjunction with other therapies for treating benign and malignant tumors and other unwanted or harmful cellular growths.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 1: Shows the complete amino acid [SEQ ID NO: 1] sequence and nucleic acid [SEQ ID NO: 53] sequence of the AD7C-NTP gene and the AD7C-NTP protein product of that gene (Sequences 120 and 121 from U.S. Pat. Nos. 5,830,670, 5,948,634, and 5,948,888; de la Monte et al., *J. Clin. Invest,.* 100:3093–3104 (1997); NCBI Entrez-Protein Accession # AAC08737; PID g30025277.

FIG. 2: Shows the complete amino acid sequences of the 122 amino acid neural thread protein (Sequence 40 from U.S. Pat. Nos. 5,830,670, 5,948,634, and 5,948,888; NCBI Entrez-Protein Accession #AAE25447 PID g10048540) [SEQ ID NO: 2].

FIG. 3: Shows the complete amino acid sequences of the 112 amino acid neural thread protein (NCBI Entrez-Protein Accession #XP_032307 PID g15928971) [SEQ ID NO: 3].

FIG. 4: Shows the complete amino acid sequences of a 106 amino acid neural thread protein-like protein (NCBI Entrez-Protein Accession #AAH14951 PID g15928971) [SEQ ID NO. 4].

FIG. 5: Shows the complete amino acid sequences of a 106 amino acid neural thread protein-like protein (NCBI Entrez-Protein Accession #XP_039102 PID g18599339) [SEQ ID NO. 5].

FIG. 6: Shows the complete amino acid sequences of the 98 amino acid neural thread protein (Sequence 30 from U.S. Pat. Nos. 5,830,670, 5,948,634, and 5,948,888; NCBI Entrez-Protein Accession #AAE25445, PID g10048538) [SEQ ID NO. 6].

FIG. 7: Shows the complete amino acid sequences of the 75 amino acid neural thread protein (Sequence 48 from U.S. Pat. Nos. 5,830,670, 5,948,634, and 5,948,888; NCBI Entrez-Protein Accession #AAE25448, PID g10048541) [SEQ ID NO. 7].

FIG. 8: Shows the complete amino acid sequences of the 68 amino acid neural thread protein (Sequence 36 from U.S. Pat. Nos. 5,830,670, 5,948,634, and 5,948,888; NCBI Entrez-Protein Accession #AAE25446, PID g10048539) [SEQ ID NO. 8].

FIG. 9: Shows the complete amino acid sequences of the 61 amino acid neural thread protein-like protein (NCBI Entrez-Protein Accession #AAH02534, PID g12803421) [SEQ ID NO. 9].

DETAILED DESCRIPTION OF THE PREFERRED EMBODIMENTS

The term "AD7C-NTP" refers to the ~41 kD protein and the gene and the nucleic acid sequences coding for it described in de la Monte et al., *J. Clin. Invest.*, 100:3093–104 (1997), in Sequences 120 and 121 of U.S. Pat. Nos. 5,948,634, 5,948,888, and 5,830,670 and in Gen-Bank #AF010144, the nucleic acid and amino acid sequences for which are illustrated in FIG. 1. The term "AD7C-NTP" also includes biologically active fragments, variants, derivatives, homologues and mimetics of AD7C-NTP.

The term "NTP" or "neural thread protein" refers to neural thread proteins and related molecules (including pancreatic thread protein) and the nucleic acid sequences coding for those proteins, and includes (but is not limited to) the following proteins and the nucleic acid sequences encoding the amino acid sequences for these proteins:

(a) AD7C-NTP;

(b) the ~42, ~26, ~21, ~17, ~14, and ~8 kD species of neural thread protein as described in U.S. Pat. Nos. 5,948,634, 5,948,888, 5,830,670, and 6,071,705 and in de la Monte et al., *J. Neuropathol. Exp. Neurol.*, 55(10):1038–50 (1996), de la Monte et al., *J. Neurol. Sci.*, 138(1–2):26–35 (1996); de la Monte et al., *J. Neurol. Sci.*, 135(2):118–25 (1996), de la Monte et al., *J. Clin. Invest.*, 100:3093–3104 (1997) and de la Monte et al., *Alz. Rep.*, 2:327–332 (1999);

(c) proteins specifically recognized by monoclonal antibody #2 on deposit with the American Type Culture Collection, Manassas, Va., under accession number HB-12546 or monoclonal antibody #5 on deposit with the American Type Culture Collection, Manassas, Va., under accession number HB-12545;

(d) proteins coded by the AD7C-NTP gene;

(e) the 122 amino acid neural thread protein described in Sequence 40 from U.S. Pat. Nos. 5,830,670, 5,948,634, and 5,948,888 and listed in NCBI Entrez-Protein Accession #AAE25447, PID g10048540, the amino acid sequences for which is illustrated in FIG. 2;

(f) the 112 amino acid neural thread protein listed in NCBI Entrez-Protein Accession #XP_032307, PID g14725132, the amino acid sequences for which is illustrated in FIG. 3;

(g) a 106 amino acid neural thread protein-like protein listed in NCBI Entrez-Protein Accession #AAH14951 PID g15928971, the amino acid sequences for which is illustrated in FIG. 4;

(h) a 106 amino acid neural thread protein-like protein listed in NCBI Entrez-Protein Accession #XP_039102, PID g18599339, the amino acid sequence for which is illustrated in FIG. 5;

(i) the 98 amino acid neural thread protein described in Sequence 30 from U.S. Pat. Nos. 5,830,670, 5,948,634, and 5,948,888 and listed in NCBI Entrez-Protein Accession # AAE25445, PID g10048538, the amino acid sequences for which is illustrated in FIG. 6;

(j) the 75 amino acid neural thread protein described in Sequence 48 from U.S. Pat. Nos. 5,830,670, 5,948,634, and 5,948,888 and listed in NCBI Entrez-Protein Accession #AAE25448, PID g10048541, the amino acid sequences for which is illustrated in FIG. 7;

(k) the 68 amino acid neural thread protein described in Sequence 36 from U.S. Pat. Nos. 5,830,670, 5,948,634, and 5,948,888 and listed in NCBI Entrez-Protein Accession #AAE25446, PID g10048539, the amino acid sequences for which is illustrated in FIG. 8;

(l) the 61 amino acid neural thread protein-like protein listed in NCBI Entrez-Protein Accession #AAH02534, PID g12803421, the amino acid sequences for which is illustrated in FIG. 9;

(m) pancreatic thread protein;

(n) the neural pancreatic thread protein (nPTP) described in U.S. Pat. No. 6,071,705; and (o) proteins specifically recognized by the antibodies produced by a hybridoma from the group consisting of HB 9934, HB 9935, and HB 9936 deposited at the American Type Culture Collection.

The term "NTP" also includes biologically active fragments, variants, derivatives, homologues and peptide mimetics of NTP.

The term "biologically active" refers to a protein, polypeptide fragment, variant, derivative, homologue or peptide mimetic which has the ability of destroying and hence either facilitating the removal of or inhibiting the further growth of harmful or unwanted cells and tissue and includes (but not limited to) the ability to kill or decrease the viability of cells in the cell culture cytotoxicity assay of Example 1 herein, the ability to cause cell loss and/or tissue necrosis in the in vivo tissue assay of Example 2 herein, or the ability to cause cell loss, tissue necrosis or tumor shrinkage in the tumor assay of Example 3 herein.

Amino acids and amino acid residues described herein may be referred to according to the accepted one or three-letter code provided in the table below.

TABLE 1

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |

TABLE 1-continued

| Amino Acid | One-Letter Symbol | Three-Letter Symbol |
|---|---|---|
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The term "NTP peptide" refers to peptides including amino acid sequences corresponding to at least a part of the amino acid sequence of NTP, preferably AD7C-NTP, and fragments of NTP, preferably AD7C-NTP, and includes homologues, derivatives, variants, fusion proteins, and peptide mimetics of such peptides. The expression "amino acid sequence" denotes at least two, and preferably more than three adjacent amino acids, and thus, the NTP-peptide will have at least two and preferably more adjacent amino acids that are the same or similar to the same adjacent amino acids in the sequence of NTP. The term "NTP peptide" also includes (but is not limited to) the following peptides derived from the amino acid sequence for AD7C-NTP as described by the amino acid sequences listed below:

NTP peptide #1 [SEQ ID NO.10], AD7C-NTP p1–15
MEFSLLLPRLECNGA
Met-Glu-Phe-Ser-Leu-Leu-Leu-Pro-Arg-Leu-Glu-Cys-Asn-Gly-Ala NTP peptide #2 [SEQ ID NO.11], AD7C-NTP p14–28
GAISAHRNLRLPGSS
Gly-Ala-Ile-Ser-Ala-His-Arg-Asn-Leu-Arg-Leu-Pro-Gly-Ser-Ser NTP peptide #3 [SEQ ID NO.12], AD7C-NTP p29–45
DSPASASPVAGITGMCT
Asp-Ser-Pro-Ala-Ser-Ala-Ser-Pro-Val-Ala-Gly-Ile-Thr-Gly-Met-Cys-Thr NTP peptide #4 [SEQ ID NO.13], AD7C-NTP p43–58
MCTHARLILYFFLVEM
Met-Cys-Thr-His-Ala-Arg-Leu-Ile-Leu-Tyr-Phe-Phe-Leu-Val-Glu-Met NTP peptide #5 [SEQ ID NO.14], AD7C-NTP p52–62
YFFLVEMEFLH
Tyr-Phe-Phe-Leu-Val-Glu-Met-Glu-Phe-Leu-His NTP peptide #6 [SEQ ID NO.15], AD7C-NTP p63–73
VGQAGLELPTS
Val-Gly-Gln-Ala-Gly-Leu-Glu-Leu-Pro-Thr-Ser NTP peptide #7 [SEQ ID NO.16], AD7C-NTP p74–90
DDPSVSASQSARYRTGH
Asp-Asp-Pro-Ser-Val-Ser-Ala-Ser-Gln-Ser-Ala-Arg-Tyr-Arg-Thr-Gly-His NTP peptide #8 [SEQ ID NO.17], AD7C-NTP p88–101
TGHHARLCLANFCG
Thr-Gly-His-His-Ala-Arg-Leu-Cys-Leu-Ala-Asn-Phe-Cys-Gly NTP peptide #9 [SEQ ID NO.18], AD7C-NTP p97–113
ANFCGRNRVSLMCPSWS
Ala-Asn-Phe-Cys-Gly-Arg-Asn-Arg-Val-Ser-Leu-Met-Cys-Pro-Ser-Trp-Ser NTP peptide #10 [SEQ ID NO.19], AD7C-NTP p114–132
PELKQSTCLSLPKCWDYRR
Pro-Glu-Leu-Lys-Gln-Ser-Thr-Cys-Leu-Ser-Leu-Pro-Lys-Cys-Trp-Asp-Tyr-Arg-Arg NTP peptide #11 [SEQ ID NO.20], AD7C-NTP p116–132
LKQSTCLSLPKCWDYRR
Leu-Lys-Gln-Ser-Thr-Cys-Leu-Ser-Leu-Pro-Lys-Cys-Trp-Asp-Tyr-Arg-Arg NTP peptide #12 [SEQ ID NO.21], AD7C-NTP p119–132
STCLSLPKCWDYRR
Ser-Thr-Cys-Leu-Ser-Leu-Pro-Lys-Cys-Trp-Asp-Tyr-Arg-Arg NTP peptide #13 [SEQ ID NO.22], AD7C-NTP p122–132
LSLPKCWDYRR
Leu-Ser-Leu-Pro-Lys-Cys-Trp-Asp-Tyr-Arg-Arg NTP peptide #14 [SEQ ID NO.23], AD7C-NTP p126–138
KCWDYRRAAVPGL
Lys-Cys-Trp-Asp-Tyr-Arg-Arg-Ala-Ala-Val-Pro-Gly-Leu NTP peptide #15 [SEQ ID NO. 24], AD7C-NTP p126–144
KCWDYRRAAVPGLFILFFL
Lys-Cys-Trp-Asp-Tyr-Arg-Arg-Ala-Ala-Val-Pro-Gly-Leu-Phe-Ile-Leu-Phe-Phe-Leu NTP peptide #16 [SEQ ID NO.25], AD7C-NTP p126–149
KCWDYRRAAVPGLFILFFLRHRCP
Lys-Cys-Trp-Asp-Tyr-Arg-Arg-Ala-Ala-Val-Pro-Gly-Leu-Phe-Ile-Leu-Phe-Phe-Leu-Arg-His-Arg-Cys-Pro NTP peptide #17 [SEQ ID NO.26], AD7C-NTP p126–163
KCWDYRRAAVPGLFILFFLRHRCPTLTQDEVQWCDHSS
Lys-Cys-Trp-Asp-Tyr-Arg-Arg-Ala-Ala-Val-Pro-Gly-Leu-Phe-Ile-Leu-Phe-Phe-Leu-Arg-His-Arg-Cys-Pro-Thr-Leu-Thr-Gln-Asp-Glu-Val-Gln-Trp-Cys-Asp-His-Ser-Ser NTP peptide #18 [SEQ ID NO.27], AD7C-NTP p128–132, p241–245
WDYRR
Trp-Asp-Tyr-Arg-Arg NTP peptide #19 [SEQ ID NO.28], AD7C-NTP p139–151
FILFFLRHRCPTL
Phe-Ile-Leu-Phe-Phe-Leu-Arg-His-Arg-Cys-Pro-Thr-Leu NTP peptide #20 [SEQ ID NO.29], AD7C-NTP p139–163
FILFFLRHRCPTLTQDEVQWCDHSS
Phe-Ile-Leu-Phe-Phe-Leu-Arg-His-Arg-Cys-Pro-Thr-Leu-Thr-Gln-Asp-Glu-Val-Gln-Trp-Cys-Asp-His-Ser-Ser NTP peptide #21 [SEQ ID NO.30], AD7C-NTP p146–174
HRCPTLTQDEVQWCDHSSLQPSTPEIKHP
His-Arg-Cys-Pro-Thr-Leu-Thr-Gln-Asp-Glu-Val-Gln-Trp-Cys-Asp-His-Ser-Ser-Leu-Gln-Pro-Ser-Thr-Pro-Glu-Ile-Lys-His-Pro NTP peptide #22 [SEQ ID NO.31], AD7C-NTP p175–188
PASASQVAGTKDMH
Pro-Ala-Ser-Ala-Ser-Gln-Val-Ala-Gly-Thr-Lys-Asp-Met-His NTP peptide #23 [SEQ ID NO.31], AD7C-NTP p186–203
DMHHYTWLIFIFIFNFLR
Asp-Met-His-His-Tyr-Thr-Trp-Leu-Ile-Phe-Ile-Phe-Ile-Phe-Asn-Phe-Leu-Arg NTP peptide #24 [SEQ ID NO.33], AD7C-NTP p189–207
HYTWLIFIFIFNFLRQSLN
His-Tyr-Thr-Trp-Leu-Ile-Phe-Ile-Phe-Ile-Phe-Asn- -continued
Phe-Leu-Arg-Gln-Ser-Leu-Asn NTP peptide #25 [SEQ ID NO.34], AD7C-NTP p208–252
SVTQAGVQWRNLGSLQPLPPGFKLFSCPSLLSSWDYRRPPRLANF
Ser-Val-Thr-Gln-Ala-Gly-Val-Gln-Trp-Arg-Asn-Leu-
Gly-Ser-Leu-Gln-Pro-Leu-Pro-Pro-Gly-Phe-Lys-Leu-
Phe-Ser-Cys-Pro-Ser-Leu-Leu-Ser-Ser-Trp-Asp-Tyr-
Arg-Arg-Pro-Pro-Arg-Leu-Ala-Asn-Phe NTP peptide #26 [SEQ ID NO.35], AD7C-NTP p227–245
PGFKLFSCPSLLSSWDYRR
Pro-Gly-Phe-Lys-Leu-Phe-Ser-Cys-Pro-Ser-Leu-Leu-
Ser-Ser-Trp-Asp-Tyr-Arg-Arg NTP peptide #27 [SEQ ID NO.36], AD7C-NTP p229–252
FKLFSCPSLLSSWDYRRPPRLANF
Phe-Lys-Leu-Phe-Ser-Cys-Pro-Ser-Leu-Leu-Ser-Ser-
Trp-Asp-Tyr-Arg-Arg-Pro-Pro-Arg-Leu-Ala-Asn-Phe NTP peptide #28 [SEQ ID NO.37], AD7C-NTP p232–245
FSCPSLLSSWDYRR
Phe-Ser-Cys-Pro-Ser-Leu-Leu-Ser-Ser-Trp-Asp-Tyr-
Arg-Arg NTP peptide #29 [SEQ ID NO.38], AD7C-NTP p236–245
SLLSSWDYRR
Ser-Leu-Leu-Ser-Ser-Trp-Asp-Tyr-Arg-Arg NTP peptide #30 [SEQ ID NO.39], AD7C-NTP p239–243,
p339–343
SSWDY
Ser-Ser-Trp-Asp-Tyr NTP peptide #31 [SEQ ID NO.40], AD7C-NTP p239–245
SSWDYRR
Ser-Ser-Trp-Asp-Tyr-Arg-Arg NTP peptide #32 [SEQ ID NO.41], AD7C-NTP p239–263
SSWDYRRPPRLANFFVFLVEMGFTM
Ser-Ser-Trp-Asp-Tyr-Arg-Arg-Pro-Pro-Arg-Leu-Ala-
Asn-Phe-Phe-Vat-Phe-Leu-Val-Glu-Met-Gly-Phe-Thr-
Met NTP peptide #33 [SEQ ID NO.42], AD7C-NTP p253–263
FVFLVEMGFTM
Phe-Val-Phe-Leu-Val-Glu-Met-Gly-Phe-Thr-Met NTP peptide #34 [SEQ ID NO.43], AD7C-NTP p259–281
MGFTMFARLILISGPCDLPASAS
Met-Gly-Phe-Thr-Met-Phe-Ala-Arg-Leu-Ile-Leu-Ile-
Ser-Gly-Pro-Cys-Asp-Leu-Pro-Ala-Ser-Ala-Ser NTP peptide #35 [SEQ ID NO.44], AD7C-NTP p270–274
ISGPC
Ile-Ser-Gly-Pro-Cys NTP peptide #36 [SEQ ID NO.45], AD7C-NTP p275–291
DLPASASQSAGITGVSH
Asp-Leu-Pro-Ala-Ser-Ala-Ser-Gln-Ser-Ala-Gly-Ile-
Thr-Gly-Val-Ser-His NTP peptide #37 [SEQ ID NO.46], AD7C-NTP p288–304
GVSHHARLIFNFCLFEM
Gly-Val-Ser-His-His-Arg-Leu-Ile-Phe-Asn-Phe-Cys-
Leu-Phe-Glu-Met NTP peptide #38 [SEQ ID NO.47], AD7C-NTP p298–307
NFCLFEMESH
Asn-Phe-Cys-Leu-Phe-Glu-Met-Glu-Ser-His NTP peptide #39 [SEQ ID NO.48], AD7C-NTP p308–353
SVTQAGVQWPNLGSLQPLPPGLKRFSCLSLPSSWDYGHLPPHPANF
Ser-Val-Thr-Gln-Ala-Gly-Val-Gln-Trp-Pro-Asn-Leu-
Gly-Ser-Leu-Gln-Pro-Leu-Pro-Pro-Gly-Leu-Lys-Arg-
Phe-Ser-Cys-Leu-Ser-Leu-Pro-Ser-Ser-Trp-Asp-Tyr-
Gly-His-Leu-Pro-Pro-His-Pro-Ala-Asn-Phe NTP peptide #40 [SEQ ID NO.49], AD7C-NTP p326–344
PPGLKRFSCLSLPSSWDYG
Pro-Pro-Gly-Leu-Lys-Arg-Phe-Ser-Cys-Leu-Ser-Leu- -continued
Pro-Ser-Ser-Trp-Asp-Tyr-Gly NTP peptide #41 [SEQ ID NO.50], AD7C-NTP p332–345
FSCLSLPSSWDYGH
Phe-Ser-Cys-Leu-Ser-Leu-Pro-Ser-Ser-Trp-Asp-Tyr-
Gly-His NTP peptide #42 [SEQ ID NO.51], AD7C-NTP p335–343
LSLPSSWDY
Leu-Ser-Leu-Pro-Ser-Ser-Trp-Asp-Tyr-Gly NTP peptide #43 [SEQ ID NO.52], AD7C-NTP p339–375
SSWDYGHLPPHPANFCIFIRGGVSPYLSGWSQTPDLR
Ser-Ser-Trp-Asp-Tyr-Gly-His-Leu-Pro-Pro-His-Pro-
Ala-Asn-Phe-Cys-Ile-Phe-Ile-Arg-Gly-Gly-Val-Ser-
Pro-Tyr-Leu-Ser-Gly-Trp-Ser-Gln-Thr-Pro-Asp-Leu-
Arg The term "fragment" refers to a protein or polypeptide that includes of a continuous subsequence of the amino acid sequence of a NTP protein or NTP peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same NTP protein or NTP peptide, with a contiguous amino acid sequence in common or not, joined together, either directly or through a linker.

The term "variant" refers to a protein or polypeptide in which one or more amino acid substitutions, deletions, and/or insertions are present as compared to the amino acid sequence of an NTP protein or NTP peptide and includes naturally occurring allelic variants or alternative splice variants of an NTP protein or NTP peptide. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, *Sequence Analysis in Molecular Biology*, p. 123–39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 2 below.

TABLE 2

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |

TABLE 2-continued

Conservative Amino Acid Substitutions leucine
isoleucine

Table 3 sets out another scheme of amino acid substitution:

TABLE 3

| Original Residue | Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Other variants can include less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site (s), or those designed to delete an existing glycosylation and/or phosphorylation site(s). Variants include at least one amino acid substitution at a glycosylation site, a proteolytic cleavage site and/or a cysteine residue. Variants also include NTP proteins or NTP peptides with additional amino acid residues before or after the NTP or NTP peptide amino acid sequence on linker peptides. For example, a cysteine residue may be added at both the amino and carboxy terminals of a NTP peptide in order to allow the cyclisation of the NTP peptide by the formation of a di-sulphide bond. The term "variant" also encompasses polypeptides that have the amino acid sequence of a NTP peptide with at least one and up to 25 additional amino acids flanking either the 3' or 5' end of the NTP peptide.

The term "derivative" refers to a chemically modified protein or polypeptide that has been chemically modified either by natural processes, such as processing and other post-translational modifications, but also by chemical modification techniques, such as for example, by addition of one or more polyethylene glycol molecules, sugars, phosphates, and/or other such molecules, where the molecule or molecules are not naturally attached to wild-type NTP proteins or peptides. Derivatives include salts. Such chemical modifications are well described in basic texts and in more detailed monographs, as well as in voluminous research literature, and they are well known to those of skill in the art. It will be appreciated that the same type of modification may be present in the same or varying degree at several sites in a given protein or polypeptide. Also, a given protein or polypeptide may contain many types of modifications.

Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *Proteins—Structure And Molecular Properties*, 2nd Ed., T. E. Creighton, W. H. Freeman and Company, New York (1993) and Wold, F., "Posttranslational Protein Modifications: Perspectives and Prospects," pgs. 1–12 in *Posttranslational Covalent Modification Of Proteins*, B. C. Johnson, Ed., Academic Press, New York (1983); Seifter et al., *Meth. Enzymol.* 182:626–646 (1990) and Rattan et al., "Protein Synthesis: Posttranslational Modifications and Aging," Ann. N.Y. Acad. Sci. 663: 48–62 (1992). The term "derivatives" includes chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein that is at least 75 percent identical in its amino acid sequence of an NTP protein, AD7C-NTP or NTP peptide, as the case may be, as determined by standard methods that are commonly used to compare the similarity in position of the amino acids of two polypeptides. The degree of similarity or identity between two proteins can be readily calculated by known methods, including but not limited to those described in *Computational Molecular Biology*, Lesk, A. M., ed., Oxford University Press, New York, 1988; *Biocomputing: Informatics and Genome Projects*, Smith, D. W., ed., Academic Press, New York, 1993; Computer Analysis of Sequence Data, Part I, Griffin, A. M., and Griffin, H. G., eds., Humana Press, New Jersey, 1994; *Sequence Analysis in Molecular Biology*, von Heinje, G., Academic Press, 1987; Sequence Analysis Primer, Gribskov, M. and Devereux, J., eds., M Stockton Press, New York, 1991; and Carillo H. and Lipman, D., SIAM, *J. Applied Math.*, 48: 1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., *Nucleic Acids Research,* 12(1): 387 (1984)), BLASTP, BLASTN, and FASTA, Atschul, S. F. et al., *J. Molec. Biol.,* 215: 403–410 (1990). The BLAST X program is publicly available from NCBI and other sources (BLAST Manual, Altschul, S., et al., NCBI NLM NIH Bethesda, Md. 20894; Altschul, S., et al., *J. Mol. Biol.,* 215: 403–410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3× (times) the average diagonal; the "average diagonal" is the average of the diagonal of the comparison matrix being used; the "diagonal" is the score or number assigned to each perfect amino acid by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al. in: *Atlas of Protein Sequence and Structure,* vol. 5, supp. 3 [1978] for the PAM250 comparison matrix; see Henikoff et al., *Proc. Natl. Acad. Sci USA,* 89:10915–10919 [1992] for the BLOSUM 62 comparison matrix) also may be used by the algorithm. The percent identity then is calculated by the algorithm. Homologues typically will have one or more amino acid substitutions, deletions, and/or insertions, when as compared with NTP, AD7C-NTP, or an NTP peptide.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to this invention provide a spatial arrangement of reactive chemical moieties that closely resemble the three-dimensional arrangement of active groups in the NTP protein or peptide on which the peptide mimetic is based. As a result of this similar active-site geometry, the peptide mimetic has effects on biological systems that are similar to the biological activity of the NTP protein or peptide.

The peptide mimetics of this invention preferably are substantially similar in both three-dimensional shape and biological activity to the NTP peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala$^1$-Peptide T Binding", Smith C. S. et al., *Drug Development Res.,* 15, pp. 371–379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268–270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method involves substituting peptide bonds in the NTP peptide by pseudopeptide bonds that confer resistance to proteolysis.

A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", *Escom, Leiden* (1990), pp. 722–773) and Dalpozzo, et al. (1993), *Int. J. Peptide Protein Res.,* 41:561–566, incorporated herein by reference). According to this modification, the amino acid sequences of the peptides may be identical to the sequences of a NTP peptide described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), *Int. J. Peptide Protein Res.,* 41:181–184, incorporated herein by reference in its entirety).

Thus, the amino acid sequences of these peptides may be identical to the sequences of an NTP peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of NTP peptides represent another class of peptide mimetics that retain the important structural determinants for biological activity, yet eliminate the peptide bonds, thereby conferring resistance to proteolysis (Simon, et al., 1992, *Proc. Natl. Acad. Sci. USA,* 89:9367–9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the NTP peptide may be replaced with the N-substituted glycine corresponding to the replaced amino acid.

The term "peptide mimetic" or "mimetic" also includes reverse-D peptides and enantiomers as defined below.

The term "reverse-D peptide" refers to a biologically active protein or peptide consisting of D-amino acids arranged in a reverse order as compared to the L-amino acid sequence of a NTP protein or NTP peptide. Thus, the carboxy terminal residue of an L-amino acid NTP peptide becomes the amino terminal for the D-amino acid peptide and so forth. For example, the NTP peptide, ISGPC, becomes $C_dP_dG_dS_dI_d$, where $C_d$, $G_d$, $I_d$, $P_d$, and $S_d$ are the D-amino acids corresponding to the L-amino acids, C, G, I, P, and S respectively.

The term "enantiomer" refers to a biologically active protein or peptide where one or more the L-amino acid residues in the amino acid sequence of a NTP peptide is replaced with the corresponding D-amino acid residue(s).

NTP proteins (including AD7C-NTP) and NTP peptides and fragments, variants, derivatives, homologues and mimetics encompassed by this invention can be prepared using methods known to those having ordinary skill in the art, such as recombinant DNA technology, protein synthesis and isolation of naturally occurring NTP, AD7C-NTP, NTP peptides and fragments, variants, derivatives and homologues thereof.

An NTP protein or NTP peptide can be prepared using well known recombinant DNA technology methods such as those set forth in Sambrook et al., (*Molecular Cloning: A Laboratory Manual*, Cold Spring Harbor Laboratory Press, Cold Spring Harbor, N.Y. [1989]) and/or Ausubel et al., eds., *Current Protocols in Molecular Biology*, Green Publishers Inc. and Wiley and Sons, N.Y. [1994].

A gene or cDNA encoding an NTP protein or NTP peptide may be obtained for example by screening a genomic or cDNA library, or by PCR amplification. Probes or primers useful for screening the library can be generated based on sequence information for other known genes or gene fragments from the same or a related family of genes, such as, for example, conserved motifs found in other NTP proteins. In addition, where a gene encoding an NTP protein or NTP peptide has been identified from one species, all or a portion of that gene may be used as a probe to identify homologous genes from other species. The probes or primers may be used to screen cDNA libraries from various tissue sources believed to express an NTP gene. Typically, conditions of high stringency will be employed for screening to minimize the number of false positives obtained from the screen.

Another means to prepare a gene encoding an NTP protein or NTP peptide is to employ chemical synthesis using methods well known to the skilled artisan, such as those described by Engels et al.(Angew. Chem. Intl. Ed., 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding an NTP protein or an NTP peptide will be several hundred nucleotides in length. Nucleic acids larger than about 100 nucleotides can be synthesized as several fragments using these methods. The fragments can then be ligated together to form the full length NTP protein or NTP peptide. Usually, the DNA fragment encoding the amino terminus of the protein will have an ATG, which encodes a methionine residue. This methionine may or may not be present on the mature form of the NTP protein or NTP peptide, depending on whether the protein produced in the host cell is designed to be secreted from that cell.

The gene, cDNA, or fragment thereof encoding the NTP protein or NTP peptide can be inserted into an appropriate expression or amplification vector using standard ligation techniques. The vector typically is selected to be functional in the particular host cell employed (i.e., the vector is compatible with the host cell machinery such that amplification of the gene and/or expression of the gene can occur). The gene, cDNA or fragment thereof encoding the NTP protein or NTP peptide may be amplified/expressed in prokaryotic, yeast, insect (baculovirus systems) and/or eukaryotic host cells. Selection of the host cell will depend in part on whether the NTP protein or peptide is to be glycosylated and/or phosphorylated. If so, yeast, insect, or mammalian host cells are preferable.

Typically, the vectors used in any of the host cells will contain at least a 5' flanking sequence (also referred to as a "promoter") and other regulatory elements as well as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide molecule located at the 5' or 3' end of the NTP protein coding sequence; the oligonucleotide molecule encodes polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as means for affinity purification of the NTP protein or NTP peptide from the host cell. Affinity purification can be accomplished, for example, by column chromatography using antibodies against the tag as an affinity matrix. Optionally, the tag can subsequently be removed from the purified NTP protein or NTP peptide by various means such as using certain peptidases.

The human immunoglobulin hinge and Fc region could be fused at either the N-terminus or C-terminus of the NTP protein or NTP peptide by one skilled in the art. The subsequent Fc-fusion protein could be purified by use of a Protein A affinity column. Fc is known to exhibit a long pharmacokinetic half-life in vivo and proteins fused to Fc have been found to exhibit a substantially greater half-life in vivo than the unfused counterpart. Also, fusion to the Fc region allows for dimerization/multimerization of the molecule that may be useful for the bioactivity of some molecules.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native NTP protein or peptide gene 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the NTP gene flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the NTP protein or NTP peptide. If the vector of choice does not contain an origin of replication site, one may be chemically synthesized based on a known sequence, and ligated into the vector. The transcription termination element is typically located 3' of the end of the NTP protein/peptide coding sequence and serves to terminate transcription of the NTP protein or peptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is usually necessary for translation initiation of mRNA. The element is typically located 3' to the promoter and 5' to the coding sequence of the NTP protein or NTP peptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for NTP protein or peptide to be secreted from the host cell, a signal sequence may be used to direct the NTP protein or peptide out of the host cell where it is synthesized, and the carboxy-terminal part of the protein may be deleted in order to prevent membrane anchoring. Typically, the signal sequence is positioned in the coding region of the NTP gene or cDNA, or directly at the 5' end of the NTP gene coding region. Many signal sequences have been identified, and any of them that are functional in the selected host cell may be used in conjunction with the NTP gene or cDNA. Therefore, the signal sequence may be homologous or heterologous to the NTP gene or cDNA, and may be homologous or heterologous to the NTP gene or cDNA. Additionally, the signal sequence may be chemically synthesized using methods set forth above. In most cases, secretion of the polypeptide from the host cell via the presence of a signal peptide will result in the removal of the amino terminal methionine from the polypeptide.

In many cases, transcription of the NTP gene or cDNA can be increased by the presence of one or more introns in the vector; this is particularly true where the NTP protein or NTP peptide is produced in eukaryotic host cells, especially mammalian host cells. The introns used may be naturally occurring within the NTP gene, especially where the gene used is a full length genomic sequence or a fragment thereof. Where the intron is not naturally occurring within the gene (as for most cDNAs), the intron(s) may be obtained from another source. The position of the intron with respect to the flanking sequence and the NTP gene is relatively important, as the intron must be transcribed to be effective. As such, where the NTP gene inserted into the expression vector is a cDNA molecule, the preferred position for the intron is 3' to the transcription start site, and 5' to the polyA transcription termination sequence. Preferably for NTP cDNA, the intron or introns will be located on one side or the other (i.e., 5' or 3') of the cDNA such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention may be constructed from starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra. Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those that are compatible with bacterial, insect, and mammalian host cells. Such vectors include, inter alia, pCRII, pCR3, and pcDNA3.1 (Invitrogen Company, San Diego, Calif.), pBSII (Stratagene Company, La Jolla, Calif.), pET15b (Novagen, Madison, Wis.), PGEX (Pharmacia Biotech, Piscataway, N.J.), pEGFP-N2 (Clontech, Palo Alto, Calif.), pETL (BlueBacII; Invitrogen), and pFastBacDual (Gibco/BRL, Grand Island, N.Y.).

After the vector has been constructed and a nucleic acid molecule encoding full length or truncated NTP protein or NTP peptide has been inserted into the proper site of the vector, the completed vector may be inserted into a suitable host cell for amplification and/or polypeptide expression. Host cells may be prokaryotic host cells (such as *E. coli*) or eukaryotic host cells (such as a yeast cell, an insect cell, or a vertebrate cell). The host cell, when cultured under appropriate conditions, can synthesize NTP protein or NTP peptide which can subsequently be collected from the culture medium (if the host cell secretes it into the medium) or directly from the host cell producing it (if it is not secreted).

After collection, the NTP protein or NTP peptide can be purified using methods such as molecular sieve chromatography, affinity chromatography, and the like. Selection of the host cell for NTP protein or peptide production will depend in part on whether the NTP protein or peptide is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the NTP protein or peptide that has biological activity, the NTP protein or NTP peptide may be "folded" after synthesis using appropriate chemical conditions as discussed below. Suitable cells or cell lines may be mammalian cells, such as Chinese hamster ovary cells (CHO), human embryonic kidney (HEK) 293 or 293T cells, or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, also are suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5.alpha., DH10, and MC1061) are well-known as host cells in the field of biotechnology. Various strains of *B. subtilis, Pseudomonas* spp., other *Bacillus* spp., *Streptomyces* spp., and the like also may be employed in this method. Many strains of yeast cells known to those skilled in the art are also available as host cells for expression of the polypeptides of the present invention.

Additionally, where desired, insect cell systems may be utilized in the methods of the present invention. Such systems are described for example in Kitts et al. (*Biotechniques*, 14:810–817 [1993]), Lucklow (*Curr. Opin. Biotechnol.*, 4:564–572 [1993]) and Lucklow et al. (*J. Virol.*, 67:4566–4579 [1993]). Preferred insect cells are Sf-9 and Hi5 (Invitrogen, Carlsbad, Calif.).

Insertion (also referred to as "transformation" or "transfection") of the vector into the selected host cell may be accomplished using such methods as calcium chloride, electroporation, microinjection, lipofection, or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary. Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of NTP protein or NTP peptide produced in the host cell can be evaluated using standard methods known in the art. Such methods include, without limitation, Western blot analysis, SDS-polyacrylamide gel electrophoresis, non-denaturing gel electrophoresis, HPLC separation, mass spectroscopy, mmunoprecipitation, and/or activity assays such as DNA binding gel shift assays.

If the NTP protein or NTP peptide has been designed to be secreted from the host cells, the majority of the NTP protein or peptide may be found in the cell culture medium. Proteins prepared in this way typically will not possess an amino terminal methionine, as it is removed during secretion from the cell. If the NTP protein or peptide is not secreted from the host cells, however, it will be present in the cytoplasm and/or the nucleus (for eukaryotic host cells) or in the cytosol (for gram negative bacteria host cells) and may have an amino terminal methionine.

For NTP protein or peptide situated in the host cell cytoplasm and/or nucleus, the host cells typically are first disrupted mechanically or with detergent to release the intra-cellular contents into a buffered solution. NTP protein or NTP peptide then can be isolated from this solution.

Purification of NTP protein or peptide from solution can be accomplished using a variety of techniques. If the protein has been synthesized such that it contains a tag such as hexaHistidine (NTP protein/hexaHis) or other small peptide such as FLAG (Sigma-Aldrich, St. Louis, Mich.) or calmodulin-binding peptide (Stratagene, La Jolla, Calif.) at either its carboxyl or amino terminus, it may essentially be purified in a one-step process by passing the solution through an affinity column where the column matrix has a high affinity for the tag or for the protein directly (i.e., a monoclonal antibody specifically recognizing the NTP protein or NTP peptide). For example, polyhistidine binds with great affinity and specificity to nickel, zinc and cobalt; thus immobilized metal ion affinity chromatography which employs a nickel-based affinity resin (as used in Qiagen's QIAexpress system or Invitrogen's Xpress System) or a cobalt-based affinity resin (as used in BD Biosciences-CLONTECH's Talon system) can be used for purification of NTP protein/polyHis. (See for example, Ausubel et al., eds., *Current Protocols in Molecular Biology*, Section 10.11.8, John Wiley & Sons, New York [1993]).

Where the NTP protein or NTP peptide is prepared without a tag attached, and no antibodies are available, other well known procedures for purification can be used. Such procedures include, without limitation, ion exchange chromatography, hydroxyapatite chromatography, hydrophobic interaction chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the NTP protein or NTP peptide will be found primarily intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation. If the NTP protein or NTP peptide has formed inclusion bodies in the cytosol, the inclusion bodies can often bind to the inner and/or outer cellular membranes and thus will be found primarily in the pellet material after centrifugation. The pellet material then can be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The NTP protein or NTP petide in its now soluble form can then be analyzed using gel electrophoresis, immunoprecipitation or the like.

If it is desired to isolate the NTP protein or NTP peptide, isolation may be accomplished using standard methods such as those set forth below and in Marston et al. (*Meth. Enz.*, 182:264–275 [1990]). In some cases, the NTP protein or peptide may not be biologically active upon isolation. Various methods for "refolding" or converting the polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. In most cases, the refolding/oxidation solution will also contain a reducing agent or the reducing agent plus its, oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, 2-mercaptoethanol(bME)/dithio-b(ME). In many instances a cosolvent is necessary to increase the efficiency of the refolding and the more common reagents used for this purpose include glycerol, polyethylene glycol of various molecular weights, and arginine.

If NTP protein or peptide inclusion bodies are not formed to a significant degree in the host cell, the NTP protein or peptide will be found primarily in the supernatant after centrifugation of the cell homogenate, and the NTP protein or NTP peptide can be isolated from the supernatant using methods such as those set forth below.

In those situations where it is preferable to partially or completely isolate the NTP protein or NTP peptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying NTP protein and NTP peptide using recombinant DNA techniques, the NTP proteins, NTP peptides and their fragments, variants, homologues and derivatives may be prepared by chemical synthesis methods (such as solid phase peptide synthesis) using techniques known in the art such as those set forth by Merrifield et al., (*J. Am. Chem. Soc.*, 85:2149 [1963]), Houghten et al. (*Proc Natl Acad. Sci. USA*, 82:5132 [1985]), and Stewart and Young (*Solid Phase Peptide Synthesis*, Pierce Chemical Co., Rockford, Ill. [1984]). Such polypeptides may be synthesized with or without a methionine on the amino terminus. Chemically synthesized NTP proteins or NTP peptides may be oxidized using methods set forth in these references to form disulfide bridges. The NTP proteins and NTP peptides are expected to have biological activity comparable to NTP proteins or NTP peptides produced recombinantly or purified from natural sources, and thus may be used interchangeably with recombinant or natural NTP protein or peptide.

Chemically modified NTP protein and peptide compositions in which the NTP protein or NTP peptide is linked to a polymer are included within the scope of the present invention. The polymer selected typically is water soluble so that the protein to which it is attached does not precipitate in an aqueous environment, such as a physiological environment. The polymer selected may be modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of NTP protein/peptide polymers is a mixture of polymers.

In some cases, it may be desirable to prepare nucleic acid and/or amino acid variants of the naturally occurring NTP proteins or of NTP peptides. Nucleic acid variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Preferred nucleic acid variants are those containing nucleotide substitutions accounting for codon preference in the host cell that is to be used to produce the NTP protein or peptide. Such "codon optimization" can be determined via computer algorithms which incorporate codon frequency tables such as "Ecohigh.Cod" for codon preference of highly expressed bacterial genes as provided by the University of Wisconsin Package Version 9.0, Genetics Computer Group, Madison, Wis. Other useful codon frequency tables include "Celegans_high.cod", "Celegans_low.cod", "Drosophila_high.cod", "Human_high.cod", "Maize_high.cod", and "Yeast_high.cod". Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s), or those designed to delete an existing glycosylation and/or phosphorylation site(s).

NTP peptides, fragments, homologs, variants, derivatives and salts thereof can be made using conventional peptide synthesis techniques known to one of ordinary skill in the art. These techniques include chemical coupling methods (cf. Wunsch, E: "Methoden der organischen Chemie", Volume 15, Band 1+2, *Synthese von Peptiden, thime Verlag, Stuttgart* (1974), and Barrany, G.; Marrifield, R. B.: "The Peptides", eds. E. Gross, J. Meienhofer, Volume 2, Chapter 1, pp. 1–284, Academic Press (1980)), enzymatic coupling methods (cf. Widmer, F. Johansen, J. T., *Carlsberg Res. Commun.*, Vol. 44, pp. 37–46 (1979), and Kullmann, W.: "Enzymatic Peptide Synthesis", CRC Press Inc. Boca Raton, Fla. (1987), and Widmer, F., Johansen, J. T. in "Synthetic Peptides in Biology and Medicines:, eds. Alitalo, K., Partanen, P., Vatieri, A., pp. 79–86, Elsevier, Amsterdam (1985)), or a combination of chemical and enzymatic methods if this is advantageous for the process design and economy. Using the guidelines and teachings provided herein, those skilled in the art are capable of varying the peptide sequence of the NTP peptide or protein to make a homologue having the same or similar biological activity (bioactivity) as the original or native NTP peptide or protein.

It is advantageous to use a mimetic of a given NTP peptide or protein rather than the protein itself, because proteins commonly exhibit two undesirable properties: (1) poor bioavailability; and (2) short duration of action. Peptide mimetics offer a route around these two major obstacles, since the molecules concerned are small enough to be both more widely available and have a long duration of action. Furthermore, peptide mimetics are much cheaper to produce than proteins and peptides. Finally, there are problems associated with stability, storage, and immunoreactivity for proteins and peptides that are not experienced with peptide mimetics.

Thus the NTP peptides described above have utility in the development of such small chemical compounds with similar biological activities and therefore with similar therapeutic utilities. Peptide mimetics of NTP peptides can be developed using combinatorial chemistry techniques and other techniques known in the art (see e.g. Proceedings of the 20th European Peptide Symposium, ed. G. Jung, E. Bayer, pp. 289–336, and references therein).

Examples of methods of structurally modifying a peptide known in the art to create a peptide mimetic include the inversion of backbone chiral centers leading to D-amino acid residue structures that may, particularly at the N-terminus, lead to enhanced stability for proteolytic degradation without adversely affecting activity. An example is given in the paper "Tritriated D-ala$^1$-Peptide T Binding", Smith C. S. et al., *Drug Development Res.* 15, pp. 371–379 (1988).

A second method is altering cyclic structure for stability, such as N to C interchain imides and lactames (Ede et al. in Smith and Rivier (Eds.) "Peptides: Chemistry and Biology", Escom, Leiden (1991), pp. 268–270). An example of this is given in conformationally restricted thymopentin-like compounds, such as those disclosed in U.S. Pat. No. 4,457,489 (1985), Goldstein, G. et al., the disclosure of which is incorporated by reference herein in its entirety.

A third method is to substitute peptide bonds in the NTP peptide by pseudopeptide bonds that confer resistance to proteolysis. A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", *Escom, Leiden* (1990), pp. 722–773) and Dalpozzo, et al. (1993), *Int. J. Peptide Protein Res.*, 41:561–566, incorporated herein by reference). According to this modification, the amino acid sequences of the peptides may be identical to the sequences of the NTP peptides described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus.

The synthesis of peptides with one or more reduced retro-inverso pseudopeptide bonds is known in the art (Sisto (1990) and Dalpozzo, et al. (1993), cited above). Thus, peptide bonds can be replaced by non-peptide bonds that allow the peptide mimetic to adopt a similar structure, and therefore biological activity, to the original peptide. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond is a (Couder, et al. (1993), *Int. J. Peptide Protein Res.*, 41:181–184, incorporated herein by reference in its entirety). Thus, the amino acid sequences of these peptides may be identical to the sequences of an NTP peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of NTP peptides represent another class of peptide mimetics that retain the important structural determinants for biological activity, yet eliminate the peptide bonds, thereby conferring resistance to proteolysis (Simon, et al., 1992, *Proc. Natl. Acad. Sci. USA*, 89:9367–9371 and incorporated herein by reference in its entirety). Peptoids are oligomers of N-substituted glycines. A number of N-alkyl groups have been described, each corresponding to the side chain of a natural amino acid (Simon, et al. (1992), cited above and incorporated herein by reference in its entirety). Some or all of the amino acids of the NTP peptide are replaced with the N-substituted glycine corresponding to the replaced amino acid.

The development of peptide mimetics can be aided by determining the tertiary structure of the original NTP peptide by NMR spectroscopy, crystallography and/or computer-aided molecular modeling. These techniques aid in the development of novel compositions of higher potency and/or greater bioavailability and/or greater stability than the original peptide (Dean (1994), BioEssays, 16: 683–687; Cohen and Shatzmiller (1993), *J. Mol. Graph.*, 11: 166–173; Wiley and Rich (1993), *Med. Res. Rev.*, 13: 327–384; Moore (1994), *Trends Pharmacol. Sci.*, 15: 124–129; Hruby (1993), *Biopolymers*, 33: 1073–1082; Bugg et al. (1993), *Sci. Am.*, 269: 92–98, all incorporated herein by reference in their entirety).

Once a potential peptide mimetic compound is identified, it may be synthesized and assayed using the methods outlined in the examples below to assess its activity. The peptide mimetic compounds obtained by the above methods, having the biological activity of the NTP peptides and similar three-dimensional structure, are encompassed by this invention. It will be readily apparent to one skilled in the art that a peptide mimetic can be generated from any of the NTP peptides bearing one or more of the modifications described above. It will furthermore be apparent that the peptide mimetics of this invention can be further used for the development of even more potent non-peptidic compounds, in addition to their utility as therapeutic compounds.

The present invention also relates to the use of NTP peptides and their corresponding nucleic acid molecules for assays to test, either qualitatively or quantitatively, for the presence of NTP peptides, NTP proteins, NTP DNA or corresponding RNA in mammalian tissue or bodily fluid samples. NTP peptides, NTP proteins and their corresponding nucleic acid molecules may have use in the preparation in such assays, whether or not the NTP peptide, NTP protein or the encoded NTP peptide or protein show biological activity. An NTP nucleic acid sequence may be a useful source of hybridization probes to test, either qualitatively or quantitatively, for the presence of NTP DNA or corresponding RNA in mammalian tissue or bodily fluid samples. An NTP protein or peptide which is not in itself biologically active may be useful for preparing antibodies that recognize and/or bind to NTP proteins or peptides. Such antibodies may be prepared using standard methods.

Thus, antibodies that react with the NTP peptides, as well as short chain antibody fragments and other reactive fragments of such antibodies, are also contemplated as within the scope of the present invention. The antibodies may be polyclonal, monoclonal, recombinant, chimeric, single-chain and/or bispecific. Typically, the antibody or fragment thereof will either be of human origin, or will be "humanized", i.e., prepared so as to prevent or minimize an immune reaction to the antibody when administered to a patient. Preferred antibodies are human antibodies, either polyclonal or monoclonal. The antibody fragment may be any fragment that is reactive with NTP peptides of the present invention, such as, $F_{ab}$, $F_{ab'}$, etc. Also provided by this invention are the hybridomas generated by presenting any NTP peptide as an antigen to a selected mammal, followed by fusing cells (e.g., spleen cells) of the mammal with certain cancer cells to create immortalized cell lines by known techniques. The methods employed to generate such cell lines and antibodies directed against all or portions of an NTP peptide are also encompassed by this invention.

The antibodies may further be used for in vivo and in vitro diagnostic or research purposes, such as in labeled form to detect the presence of NTP protein or peptide in a body fluid or cell sample.

This invention also encompasses the use of one or more NTP peptides as calibration standards in assays that test, either qualitatively or quantitatively, for the presence of NTP peptides, NTP proteins, NTP DNA or corresponding RNA in mammalian tissue or bodily fluid samples.

The present invention is directed to novel methods of treating conditions requiring removal of cells, such as benign and malignant tumors, glandular (e.g. prostate) hyperplasia, unwanted facial hair, warts, and unwanted fatty tissue. Such a method comprises administering to a mammal in need a therapeutically effective amount of NTP peptide.

The condition can be, for example, tumors of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, lymph nodes and lymphoid system, and other organs.

As used herein, the term "malignant tumor" is intended to encompass all forms of human carcinomas, sarcomas and melanomas which occur in the poorly differentiated, moderately differentiated, and well-differentiated forms.

This invention satisfies a need in the art for treatments that can remove benign tumors with less risk and fewer of the undesirable side effects of surgery. A method for removing benign tumors in surgically hazardous areas such as in deep locations in the body (e.g., brain, heart, lungs, and others) is particularly needed.

The method of treating conditions where cells must be removed can be used in conjunction with conventional methods of treating such conditions, such as surgical excision, chemotherapy, and radiation. NTP peptides can be administered before, during, or after such conventional treatments.

The condition to be treated also can be a hyperplasia, hypertrophy, or overgrowth of a tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

Yet another condition that can be treated using the method of the invention is a virally, bacterially, or parasitically altered tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

The condition to be treated can also be a malformation of a tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

In particular, the condition to be treated can be tonsillar hypertrophy, prostatic hyperplasia or hemorrhoids. The condition to be treated can be a vascular disease, such as atherosclerosis or arteriosclerosis, or a vascular disease, such as varicose veins. The condition to be treated can also be a cosmetic modification to a tissue, such as skin, eye, ear, nose, throat, mouth, muscle, connective tissue, hair, or breast tissue.

Therapeutic compositions of NTP peptides are within the scope of the present invention. Such compositions may comprise a therapeutically effective amount of the NTP peptide in admixture with a pharmaceutically acceptable carrier. The carrier material may be water for injection, preferably supplemented with other materials common in solutions for administration to mammals. Typically, an NTP peptide for therapeutic use will be administered in the form of a composition comprising purified NTP peptide in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Compositions comprise buffers known to those having ordinary skill in the art with an appropriate range of pH values, including Tris buffer of about pH 7.0–8.5, or acetate buffer of about pH 4.0–5.5, which may further include sorbitol or a suitable substitute therefor.

The use of NTP peptides conjugated or linked or bound to an antibody, antibody fragment, antibody-like molecule, or a molecule with a high affinity to a specific tumor marker, such as a cellular receptor, signal peptide or over-expressed enzyme, for targeting to the unwanted cellular elements also is encompassed by the scope of the invention. The antibody, antibody fragment, antibody-like molecule, or molecule with a high affinity to a specific tumor marker is used to target the NTP peptide conjugate to a specific cellular or tissue target. For example, a tumor with a distinctive surface antigen or expressed antigen can be targeted by the antibody, antibody fragment, or antibody-like binding molecule and the tumor cells can be killed by the NTP peptide. Such an approach using antibody targeting has the anticipated advantages of decreasing dosage, increasing the likelihood of binding to and uptake by the target cells, and increased usefulness for targeting and treating metastatic tumors and microscopic sized tumors.

This invention also encompasses the use of NTP peptides conjugated or linked or bound to a protein or other molecule to form a composition that, upon cleavage at or near the site(s) of the tumor or other unwanted cells by a tumor- or site-specific enzyme or protease or by an antibody conjugate that targets tumor or other unwanted cells, releases the NTP peptide at or near the site(s) of the tumor or other unwanted cells This invention also encompasses the use of NTP peptides conjugated or linked or bound to a protein or other molecule to form a composition that releases the NTP peptide or some biologically active fragment of the NTP peptide upon exposure of the tissue to be treated to light (as in laser therapies or other photo-dynamic or photo-activated therapy), other forms of electromagnetic radiation such as infra-red radiation, ultraviolet radiation, x-ray or gamma ray radiation, localized heat, alpha or beta radiation, ultrasonic emissions, or other sources of localized energy.

The NTP peptides may be employed alone, together, or in combination with other pharmaceutical compositions, such as cytokines, growth factors, antibiotics, apoptotis-inducing agents, anti-inflammatories, and/or chemotherapeutic agents as is appropriate for the indication being treated.

This invention also encompasses therapeutic compositions of NTP peptides employing dendrimers, fullerenes, and other synthetic molecules, polymers and macromolecules where the NTP peptide and/or its corresponding DNA molecule is conjugated with, attached to or enclosed in the molecule, polymer or macromolecule, either by itself or in conjunction with other species of molecule such as a tumor-specific marker. For example, U.S. Pat. No. 5,714,166, Bioactive and/or Targeted Dendimer Conjugates, provides a method of preparing and using, inter alia, dendritic polymer conjugates composed of at least one dendrimer with a target director(s) and at least one bioactive agent conjugated to it.

This invention also encompasses therapeutic compositions of NTP peptides and/or genes and drug delivery vehicles such as lipid emulsions, micelle polymers, polymer microspheres, electroactive polymers, hydrogels and liposomes.

The use of NTP peptides or related genes or gene equivalents transferred to the unwanted cells is also encompassed by the scope of the invention. Overexpression of NTP peptide within the tumor can be used to induce the cells in the tumor to die and thus reduce the tumor cell population. The gene or gene equivalent transfer of NTP peptide to treat the unwanted cellular elements is anticipated to have the advantage of requiring less dosage, and of being passed on to the cellular progeny of the targeted cellular elements, thus necessitating less frequent therapy, and less total therapy. This invention also encompasses the transfer of genes that code for a fusion protein containing NTP peptide to the unwanted cells or neighboring cells where, following the expression of the gene and the production and/or secretion of the fusion protein, the fusion protein is cleaved either by native enzymes or proteases or by a prodrug to release the NTP peptide in, at or near the unwanted cells.

The use of cloned recombinant NTP peptide-antibody conjugates; cloned recombinant NTP peptide-antibody fragment conjugates; and cloned recombinant NTP peptide-antibody-like protein conjugates is also encompassed by the scope of the invention. The advantages of a cloned NTP peptide combined with targeting conjugate (such as an antibody, antibody fragment, antibody-like molecule, or a molecule with a high affinity to a cancer-specific receptor or other tumor marker) are that such a molecule combines the targeting advantages described above in addition to advantages for manufacturing and standardized production of the cloned conjugated molecule.

Solid dosage forms for oral administration include but are not limited to, capsules, tablets, pills, powders, and granules. In such solid dosage forms, the active compound is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as acetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active ingredients in the compositions of the invention may be varied to obtain a therapeutically effective amount of NTP peptide that is effective to obtain a desired therapeutic response for a particular composition and method of administration. The selected dosage level therefore depends upon the desired therapeutic effect, the route of administration, the desired duration of treatment, the size of the individual or animal treated, and other factors.

With mammals, including humans, the effective amounts can be administered on the basis of body surface area. The interrelationship of dosages for animals of various sizes, species and humans (based on mg/M² of body surface) is described by E. J. Freireich et al., *Cancer Chemother. Rep.,* 50(4):219 (1966). Body surface area may be approximately determined from the height and weight of an individual (see e.g., Scientific Tables, Geigy Pharmaceuticals, Ardsley, N.Y. pp. 537–538 (1970)). Using the techniques known to those skilled in the art, and using the guidelines and teachings provided herein, skilled artisans will be capable of determining the therapeutically effective amount of NTP peptide for use in the present invention.

The total daily dose of the NTP peptide administered to a host may be in single or divided doses. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated.

A method of administering an NTP peptide composition according to the invention includes, but is not limited to, administering the compounds intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc.

Another method of administering an NTP peptide of the invention is by a transdermal or transcutaneous route. One example of such an embodiment is the use of a patch. In particular, a patch can be prepared with a fine suspension of NTP peptide in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well. The patch can contain the NTP peptide compound in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

NTP peptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22: 547–556 [1983]), poly (2-hydroxyethyl-methacrylate) (Langer et al., *J. Biomed. Mater. Res.,* 15: 167–277 [1981] and Langer, *Chem. Tech.,* 12: 98–105 [1982]), ethylene vinyl acetate (Langer et al., supra) or poly-D(−)-3-hydroxybutyric acid (EP 133,988). Sustained-release compositions also may include liposomes, which can be prepared by any of several methods known in the art (e.g., Eppstein et al., *Proc. Natl. Acad. Sci. USA,* 82: 3688–3692 [1985]; EP 36,676; EP 88,046; and EP 143,949).

Another method of administering an NTP peptide of the invention is by direct or indirect infusion of NTP peptide into the tumor or other tissue to be treated. One example of such an embodiment is the direct injection of NTP peptide into the tumor or other tissue to be treated. The treatment may consist of a single injection, multiple injections on one occasion or a series of injections over a period of hours, days or months with the regression or destruction of the tumor or other tissue to be treated being monitored by means of biopsy, imaging or other methods of monitoring tissue growth. The injection into the tumor or other tissue to be treated may be by a device inserted into an orifice such as the nose, mouth, ear, vagina, rectum or urethra or through an incision in order to reach the tumor or tissue in vivo and may performed in conjunction with an imaging or optical system such as ultrasound or fibre optic scope in order to identify the appropriate site for the injection(s). Another example of such an embodiment is the use of a device that can provide a constant infusion of NTP peptide to the tissue over time.

Another method of administering an NTP peptide of the invention is in conjunction with a surgical or similar procedure employed to physically excise, ablate or otherwise kill or destroy tumor or other tissue or cellular elements required or desired to be removed or destroyed wherein an NTP peptide of the invention is administered to the immediate area(s) surrounding the area(s) where the tumor or other tissue was removed in order to destroy or impede the growth of any tumor cells or other cellular elements not removed or destroyed by the procedure Another method of administering an NTP peptide of the invention is by implantation of a device within the tumor or other tissue to be treated. One example of such an embodiment is the implantation of a wafer containing NTP peptide in the tumor or other tissue to be treated. The wafer releases a therapeutic dose of NTP peptide into the tissue over time. Alternatively or additionally, the composition may be administered locally via implantation into the affected area of a membrane, sponge, or other appropriate material on to which the NTP peptide has been absorbed. Where an implantation device is used, the device may be implanted into any suitable tissue or organ, and delivery of the NTP peptide may be directly through the device via bolus, or via continuous administration, or via catheter using continuous infusion.

An alternative method of administration is to introduce one or more copies of an NTP peptide-encoding gene into the cell being targeted and, if necessary, inducing the copy (ies) of the gene to begin producing NTP peptide intracellularly. One manner in which gene therapy can be applied is to use the NTP peptide-encoding gene (either genomic DNA, cDNA, and/or synthetic DNA encoding the NTP peptide or a fragment, variant, homologue or derivative thereof) which may be operably linked to a constitutive or inducible promoter to form a "gene therapy DNA construct". The promoter may be homologous or heterologous to an endogenous NTP peptide-encoding gene, provided that it is active in the cell or tissue type into which the construct will be inserted. Other components of the gene therapy DNA construct may optionally include, as required, DNA molecules designed for site-specific integration (e.g., endogenous flanking sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting) cell-specific internalization factors, and transcription factors to enhance expression by a vector as well as factors to enable vector manufacture.

Means of gene delivery to a cell or tissue in vivo or ex vivo include (but are not limited to) direct injection of bare DNA, ballistic methods, liposome-mediated transfer, receptor-mediated transfer (ligand-DNA complex), electroporation, and calcium phosphate precipitation. See U.S. Pat. No. 4,970,154, WO 96/40958, U.S. Pat. No. 5,679,559, U.S. Pat. No. 5,676,954, and U.S. Pat. No. 5,593,875, the disclosures of each of which are incorporated by reference herein in their entireties. They also include use of a viral vector such as a retrovirus, adenovirus, adeno-associated virus, pox virus, lentivirus, papilloma virus or herpes simplex virus, use of a DNA-protein conjugate and use of a liposome. The use of gene therapy vectors is described, for example, in U.S. Pat. No. 5,672,344, U.S. Pat. No. 5,399,346, U.S. Pat. No. 5,631,236, and U.S. Pat. No. 5,635,399, the disclosures of each of which are incorporated by reference herein in their entireties.

The NTP peptide-encoding gene may be delivered through implanting into patients certain cells that have been genetically engineered ex vivo, using methods such as those described herein, to express and secrete the NTP peptide or fragments, variants, homologues, or derivatives thereof. Such cells may be animal or human cells, and may be derived from the patient's own tissue or from another source, either human or non-human. Optionally, the cells may be immortalized or be stem cells. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product (s) but prevent destruction of the cells by the patient's immune system or by other detrimental factors from the surrounding tissues. Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627, the disclosures of each of which are incorporated by reference herein in their entireties. A system for encapsulating living cells is described in PCT WO 91/10425. Techniques for formulating a variety of other sustained or controlled delivery means, such as liposome carriers, bio-erodible particles or beads, are also known to those in the art, and are described, for example, in U.S. Pat. No. 5,653,975, the disclosure of which is incorporated by reference herein in its entirety. The cells, with or without encapsulation, may be implanted into suitable body tissues or organs of the patient.

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

The purpose of this example was to determine the effect of NTP peptide #43 on tissue at sites of injection.

Eight normal rats were injected in the skin and subcutaneously, each in four different foci, and in extremity skeletal muscle, each in two different foci, with NTP peptide #43 in saline in quantities of 100 to 400 mL at concentrations of 0.1–1 mg/mL delivered from plastic syringes through stainless steel 26 gauge needles.

The animals were observed for 24 hours and painlessly sacrificed at 24 hours. The 48 individual foci of infiltration were excised, fixed in 10% formalin, embedded in paraffin, and stained and examined by standard histopathological methods.

Similar groups of control rats were injected with (1) bovine serum albumin 0.1% in saline, (2) normal human serum, (3) physiological saline, (4) noninfectious bacterial proteins, and (5) control peptides and purified and then examined and sacrificed as above, with the excised foci of injection treated as above.

Results

Injection of NTP peptide # 43 produced abundant acute necrosis of tissue at the injection sites. The necrosis was evident in muscle tissue, subcutaneous connective tissue, and dermis at the sites where NTP peptide #43 was injected. At 24 hours, cells appeared pale, shrunken, and necrotic, and there was infiltration with inflammatory cells. The necrosis correlated with the areas of injection and did not appear to spread far beyond the site of injection.

Apart from the mild areas of inflammation, controls showed no evidence of necrosis or cell loss. In contrast to the NTP peptide # 43 injections where entire fields of muscle fiber layers were necrotic, the controls showed minimal or absent muscle changes. Control injections had mild to minimal acute inflammation at the injection sites and focal microhemorrhages from the needles.

EXAMPLE 2

The purpose of this example was to determine the effect of NTP peptide #17 on tissue at sites of injection.

Eight normal rats were injected in the skin and subcutaneously, each in four different foci, and in extremity skeletal muscle, each in two different foci, with NTP peptide #17 in saline in quantities of 100 to 400 mL at concentrations of 0.1–1 mg/mL delivered from plastic syringes through stainless steel 26 gauge needles.

The animals were observed for 24 hours and painlessly sacrificed at 24 hours. The 48 individual foci of infiltration were excised, fixed in 10% formalin, embedded in paraffin, and stained and examined by standard histopathological methods.

The controls were the same as Example 1.

Results

Injection of NTP peptide # 17 produced abundant acute necrosis of tissue at the injection sites. The necrosis was evident in muscle tissue, subcutaneous connective tissue, and dermis at the sites where NTP peptide #17 was injected. At 24 hours, cells appeared pale, shrunken, and necrotic, and there was infiltration with inflammatory cells. The necrosis correlated with the areas of injection and did not appear to spread far beyond the site of injection.

Apart from the mild areas of inflammation, controls showed no evidence of necrosis or cell loss. In contrast to the NTP peptide # 17 injections where entire fields of muscle fiber layers were necrotic, the controls showed minimal or absent muscle changes. Control injections had mild to minimal acute inflammation at the injection sites and focal microhemorrhages from the needles.

EXAMPLE 3

The purpose of this example was to determine the effect of NTP peptide #20 on tissue at sites of injection.

Eight normal rats were injected in the skin and subcutaneously, each in four different foci, and in extremity skeletal muscle, each in two different foci, with NTP peptide #20 in saline in quantities of 100 to 400 mL at concentrations of 0.1–1 mg/mL delivered from plastic syringes through stainless steel 26 gauge needles.

The animals were observed for 24 hours and painlessly sacrificed at 24 hours. The 48 individual foci of infiltration were excised, fixed in 10% formalin, embedded in paraffin, and stained and examined by standard histopathological methods.

The controls were the same as Example 1.

Results

Injection of NTP peptide # 20 produced cell death and necrosis of tissue at the injection sites. The cell deat was present in muscle tissue, subcutaneous connective tissue, and dermis at the sites where NTP peptide # 20 was injected. At 24 hours, cells in those areas appeared pale, shrunken, and necrotic, and there was infiltration with inflammatory cells. The cell death and necrosis was in the areas of injection and did not appear to spread far beyond the site of injection.

Apart from the mild areas of inflammation, controls showed no evidence of necrosis or cell loss. In contrast to the NTP peptide # 20 injections where entire fields of muscle fiber layers were necrotic, the controls showed minimal or absent muscle changes. Control injections had mild to minimal acute inflammation at the injection sites and occasional focal microhemorrhages from the needles.

EXAMPLE 4

The purpose of this example was to determine the effect of NTP peptide #19 on tissue at sites of injection.

Eight normal rats were injected in the skin and subcutaneously, each in four different foci, and in extremity skeletal muscle, each in two different foci, with NTP peptide #19 in saline in quantities of 100 to 400 mL at concentrations of 0.1–1 mg/mL delivered from plastic syringes through stainless steel 26 gauge needles.

The animals were observed for 24 hours and painlessly sacrificed at 24 hours. The 48 individual foci of infiltration were excised, fixed in 10% formalin, embedded in paraffin, and stained and examined by standard histopathological methods.

The controls were the same as Example 1.

Results

As in the above examples, injection of NTP peptide # 19 produced cell death and necrosis of tissue at the injection sites. Controls showed minimal or absent changes consisting of acute inflammation at the injection sites and focal microhemorrhages from the needles.

EXAMPLE 5

The purpose of this example was to determine the effect of NTP peptide #16 on tissue at sites of injection.

Eight normal rats were injected in the skin and subcutaneously, each in four different foci, and in extremity skeletal muscle, each in two different foci, with NTP peptide #16 in saline in quantities of 100 to 400 mL at concentrations of 0.1–1 mg/mL delivered from plastic syringes through stainless steel 26 gauge needles.

The animals were observed for 24 hours and painlessly sacrificed at 24 hours. The 48 individual foci of infiltration were excised, fixed in 10% formalin, embedded in paraffin, and stained and examined by standard histopathological methods.

The controls were the same as Example 1.

Results

As in the above examples, injection of NTP peptide # 16 produced cell death and necrosis of tissue at the injection sites. Controls showed minimal or absent changes consisting of acute inflammation at the injection sites and focal microhemorrhages from the needles.

EXAMPLE 6

The purpose of this example was to determine the effect of NTP peptide #15 on tissue at sites of injection.

Eight normal rats were injected in the skin and subcutaneously, each in four different foci, and in extremity skeletal muscle, each in two different foci, with NTP peptide #15 in saline in quantities of 100 to 400 mL at concentrations of 0.1–1 mg/mL delivered from plastic syringes through stainless steel 26 gauge needles.

The animals were observed for 24 hours and painlessly sacrificed at 24 hours. The 48 individual foci of infiltration were excised, fixed in 10% formalin, embedded in paraffin, and stained and examined by standard histopathological methods.

The controls were the same as Example 1.

Results

As in the above examples, injection of NTP peptide # 15 produced cell death and necrosis of tissue at the injection sites. Controls showed minimal or absent changes consisting of acute inflammation at the injection sites and focal microhemorrhages from the needles.

EXAMPLE 7

The purpose of this example was to determine the effect of NTP peptide #14 on tissue at sites of injection.

Eight normal rats were injected in the skin and subcutaneously, each in four different foci, and in extremity skeletal muscle, each in two different foci, with NTP peptide #14 in saline in quantities of 100 to 400 mL at concentrations of 0.1–1 mg/mL delivered from plastic syringes through stainless steel 26 gauge needles.

The animals were observed for 24 hours and painlessly sacrificed at 24 hours. The 48 individual foci of infiltration were excised, fixed in 10% formalin, embedded in paraffin, and stained and examined by standard histopathological methods.

The controls were the same as Example 1.

Results

As in the above examples, injection of NTP peptide # 14 produced cell death and necrosis of tissue at the injection sites. Controls showed minimal or absent changes consisting of acute inflammation at the injection sites and focal microhemorrhages from the needles.

It will be apparent to those skilled in the art that various modifications and variations can be made in the methods and compositions of the present invention without departing from the spirit or scope of the invention. Thus, it is intended that the present invention cover the modifications and variations of this invention.

What is claimed is:

1. An isolated NTP-peptide selected from the group consisting of SEQ ID NOs: 23, 24, 25, 26, 28, 29, and 52.

2. A composition comprising at least one NTP-peptide according to claim 1, and a carrier.

3. An isolated peptide consisting of a NTP-peptide according to claim 1 wherein said peptide is selected from the group consisting of SEQ ID NOs: 23, 24, 25, 26, 28, 29, and 52 fused to an antibody or an antibody fragment.

4. A method of treating a benign or malignant tumor in a mammal comprising local administration of a therapeutically effective amount of a NTP-peptide according to claim 1 to said mammal in need thereof.

5. The method according to claim 4, wherein the therapeutically effective amount of the NTP-peptide is administered by a method selected from the group consisting of orally, subcutaneously, intradermally, intranasally, intravenously, intramuscularly, intrathecally, intranasally, topically, and transdermally.

6. The method of claim 4, wherein the treatment is administered to the mammal before, during, or after treatment of the mammal with at least one treatment selected from group consisting of surgical excision, transplantation, grafting, chemotherapy, immunotherapy, vaccination, thermal or electrical ablation, cryotherapy, laser therapy, phototherapy, gene therapy, and radiation.

7. The method of claim 4, where the benign or malignant tumor is in a tissue selected from the group consisting of lung, breast, stomach, pancreas, prostate, bladder, bone, ovary, skin, kidney, sinus, colon, intestine, stomach, rectum, esophagus, head, spleen, salivary gland, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

* * * * *

SEQUENCE LISTING

<160> NUMBER OF SEQ ID NOS: 53

<210> SEQ ID NO 1
<211> LENGTH: 375
<212> TYPE: PRT
<213> ORGANISM: Homo sapiens

<400> SEQUENCE: 1

```
Met Glu Phe Ser Leu Leu Pro Arg Leu Glu Cys Asn Gly Ala Ile
 1               5                  10                  15

Ser Ala His Arg Asn Leu Arg Leu Pro Gly Ser Ser Asp Ser Pro Ala
                20                  25                  30

Ser Ala Ser Pro Val Ala Gly Ile Thr Gly Met Cys Thr His Ala Arg
                35                  40                  45

Leu Ile Leu Tyr Phe Phe Leu Val Glu Met Glu Phe Leu His Val Gly
            50                  55                  60

Gln Ala Gly Leu Glu Leu Pro Thr Ser Asp Asp Pro Ser Val Ser Ala
 65                  70                  75                  80

Ser Gln Ser Ala Arg Tyr Arg Thr Gly His His Ala Arg Leu Cys Leu
                85                  90                  95

Ala Asn Phe Cys Gly Arg Asn Arg Val Ser Leu Met Cys Pro Ser Trp
                100                 105                 110

Ser Pro Glu Leu Lys Gln Ser Thr Cys Leu Ser Leu Pro Lys Cys Trp
                115                 120                 125

Asp Tyr Arg Arg Ala Ala Val Pro Gly Leu Phe Ile Leu Phe Phe Leu
                130                 135                 140

Arg His Arg Cys Pro Thr Leu Thr Gln Asp Glu Val Gln Trp Cys Asp
145                 150                 155                 160

His Ser Ser Leu Gln Pro Ser Thr Pro Glu Ile Lys His Pro Ala
                165                 170                 175

Ser Ala Ser Gln Val Ala Gly Thr Lys Asp Met His His Tyr Thr Trp
                180                 185                 190

Leu Ile Phe Ile Phe Ile Phe Asn Phe Leu Arg Gln Ser Leu Asn Ser
                195                 200                 205

Val Thr Gln Ala Gly Val Gln Trp Arg Asn Leu Gly Ser Leu Gln Pro
                210                 215                 220

Leu Pro Pro Gly Phe Lys Leu Phe Ser Cys Pro Ser Leu Leu Ser Ser
225                 230                 235                 240

Trp Asp Tyr Arg Arg Pro Pro Arg Leu Ala Asn Phe Phe Val Phe Leu
                245                 250                 255

Val Glu Met Gly Phe Thr Met Phe Ala Arg Leu Ile Leu Ile Ser Gly
                260                 265                 270

Pro Cys Asp Leu Pro Ala Ser Ala Ser Gln Ser Ala Gly Ile Thr Gly
                275                 280                 285

Val Ser His His Ala Arg Leu Ile Phe Asn Phe Cys Leu Phe Glu Met
                290                 295                 300

Glu Ser His Ser Val Thr Gln Ala Gly Val Gln Trp Pro Asn Leu Gly
305                 310                 315                 320

Ser Leu Gln Pro Leu Pro Pro Gly Leu Lys Arg Phe Ser Cys Leu Ser
                325                 330                 335

Leu Pro Ser Ser Trp Asp Tyr Gly His Leu Pro Pro His Pro Ala Asn
                340                 345                 350

Phe Cys Ile Phe Ile Arg Gly Gly Val Ser Pro Tyr Leu Ser Gly Trp
```

```
                    355                 360                 365
Ser Gln Thr Pro Asp Leu Arg
        370                 375

<210> SEQ ID NO 2
<211> LENGTH: 122
<212> TYPE: PRT
<213> ORGANISM: Homo sapiens

<400> SEQUENCE: 2

Met Met Val Cys Trp Asn Arg Phe Gly Lys Trp Val Tyr Phe Ile Ser
  1               5                  10                  15

Ala Ile Phe Asn Phe Gly Pro Arg Tyr Leu Tyr His Gly Val Pro Phe
             20                  25                  30

Tyr Phe Leu Ile Leu Val Arg Ile Ile Ser Phe Leu Ile Gly Asp Met
         35                  40                  45

Glu Asp Val Leu Leu Asn Cys Thr Leu Leu Lys Arg Ser Ser Arg Phe
 50                  55                  60

Arg Phe Trp Gly Ala Leu Val Cys Ser Met Asp Ser Cys Arg Phe Ser
 65                  70                  75                  80

Arg Val Ala Val Thr Tyr Arg Phe Ile Thr Leu Leu Asn Ile Pro Ser
                 85                  90                  95

Pro Ala Val Trp Met Ala Arg Asn Thr Ile Asp Gln Gln Val Leu Ser
            100                 105                 110

Arg Ile Lys Leu Glu Ile Lys Arg Cys Leu
        115                 120

<210> SEQ ID NO 3
<211> LENGTH: 112
<212> TYPE: PRT
<213> ORGANISM: Homo sapiens

<400> SEQUENCE: 3

Met Ala Gln Ser Arg Leu Thr Ala Thr Ser Ala Ser Arg Val Gln Ala
  1               5                  10                  15

Ile Leu Leu Ser Gln Pro Pro Lys Gln Leu Gly Leu Arg Ala Pro Ala
             20                  25                  30

Asn Thr Pro Leu Ile Phe Val Phe Ser Leu Glu Ala Gly Phe His His
         35                  40                  45

Ile Cys Gln Ala Gly Leu Lys Leu Leu Thr Ser Gly Asp Pro Pro Ala
 50                  55                  60

Ser Ala Phe Gln Ser Ala Gly Ile Thr Gly Val Ser His Leu Thr Gln
 65                  70                  75                  80

Pro Ala Asn Leu Asp Lys Lys Ile Cys Ser Asn Gly Gly Ser Cys Tyr
                 85                  90                  95

Val Ala Gln Ala Gly Leu Lys Leu Leu Ala Ser Cys Asn Pro Ser Lys
            100                 105                 110

<210> SEQ ID NO 4
<211> LENGTH: 106
<212> TYPE: PRT
<213> ORGANISM: Homo sapiens

<400> SEQUENCE: 4

Met Trp Thr Leu Lys Ser Ser Leu Val Leu Leu Leu Cys Leu Thr Cys
  1               5                  10                  15

Ser Tyr Ala Phe Met Phe Ser Ser Leu Arg Gln Lys Thr Ser Glu Pro
             20                  25                  30
```

```
Gln Gly Lys Val Pro Cys Gly Glu His Phe Arg Ile Arg Gln Asn Leu
            35                  40                  45

Pro Glu His Thr Gln Gly Trp Leu Gly Ser Lys Trp Leu Trp Leu Leu
 50                      55                  60

Phe Ala Val Val Pro Phe Val Ile Leu Lys Cys Gln Arg Asp Ser Glu
 65                  70                  75                  80

Lys Asn Lys Val Arg Met Ala Pro Phe Leu His His Ile Asp Ser
                85                  90                  95

Ile Ser Gly Val Ser Gly Lys Arg Met Phe
                100                 105

<210> SEQ ID NO 5
<211> LENGTH: 106
<212> TYPE: PRT
<213> ORGANISM: Homo sapiens

<400> SEQUENCE: 5

Met Phe Phe Val Leu Tyr Arg Phe Cys Phe Phe Glu Thr Glu
 1               5                  10                  15

Ser His Ser Leu Thr Gln Ala Gly Val Gln Trp Cys Glu Leu Gly Ser
                20                  25                  30

Pro Gln Pro Leu Pro Ser Gly Phe Lys Arg Phe Ser Cys Leu Ser Leu
            35                  40                  45

Leu Ser Ser Trp Asp Tyr Ser His Glu Pro Pro His Pro Val Ile Cys
 50                      55                  60

Ser Phe Leu Met Glu Lys Cys Leu Ile Leu Tyr Lys Pro Asn Gly Asp
 65                  70                  75                  80

Thr Ile Gly Pro Ile Leu Val Gln Gln Gly Lys Arg Gln Lys Leu Tyr
                85                  90                  95

Ile Ser Ala Asp Leu Val His Leu Ile Ala
                100                 105

<210> SEQ ID NO 6
<211> LENGTH: 98
<212> TYPE: PRT
<213> ORGANISM: Homo sapiens

<400> SEQUENCE: 6

Glu Ala Tyr Tyr Thr Met Leu His Leu Pro Thr Thr Asn Arg Pro Lys
 1               5                  10                  15

Ile Ala His Cys Ile Leu Phe Asn Gln Pro His Ser Pro Arg Ser Asn
                20                  25                  30

Ser His Ser His Pro Asn Pro Leu Lys Leu His Arg Arg Ser His Ser
            35                  40                  45

His Asn Arg Pro Arg Ala Tyr Ile Leu Ile Thr Ile Leu Pro Ser Lys
 50                      55                  60

Leu Lys Leu Arg Thr His Ser Gln Ser His His Asn Pro Leu Ser Arg
 65                  70                  75                  80

Thr Ser Asn Ser Thr Pro Thr Asn Ser Phe Leu Met Thr Ser Ser Lys
                85                  90                  95

Pro Arg

<210> SEQ ID NO 7
<211> LENGTH: 75
<212> TYPE: PRT
<213> ORGANISM: Homo sapiens
```

```
<400> SEQUENCE: 7

Ser Ser Ser Leu Gly Leu Pro Lys Cys Trp Asp Tyr Arg His Glu Leu
 1               5                  10                  15

Leu Ser Leu Ala Leu Met Ile Asn Phe Arg Val Met Ala Cys Thr Phe
            20                  25                  30

Lys Gln His Ile Glu Leu Arg Gln Lys Ile Ser Ile Val Pro Arg Lys
        35                  40                  45

Leu Cys Cys Met Gly Pro Val Cys Pro Val Lys Ile Ala Leu Leu Thr
    50                  55                  60

Ile Asn Gly His Cys Thr Trp Leu Pro Ala Ser
 65                 70                  75

<210> SEQ ID NO 8
<211> LENGTH: 68
<212> TYPE: PRT
<213> ORGANISM: Homo sapiens

<400> SEQUENCE: 8

Met Phe Val Phe Cys Leu Ile Leu Asn Arg Glu Lys Ile Lys Gly Gly
 1               5                  10                  15

Asn Ser Ser Phe Phe Leu Leu Ser Phe Phe Ser Phe Gln Asn Cys
            20                  25                  30

Cys Gln Cys Phe Gln Cys Arg Thr Thr Glu Gly Tyr Ala Val Glu Cys
        35                  40                  45

Phe Tyr Cys Leu Val Asp Lys Ala Ala Phe Glu Cys Trp Trp Phe Tyr
    50                  55                  60

Ser Phe Asp Thr
 65

<210> SEQ ID NO 9
<211> LENGTH: 61
<212> TYPE: PRT
<213> ORGANISM: Homo sapiens

<400> SEQUENCE: 9

Met Glu Pro His Thr Val Ala Gln Ala Gly Val Pro Gln His Asp Leu
 1               5                  10                  15

Gly Ser Leu Gln Ser Leu Leu Pro Arg Phe Lys Arg Phe Ser Cys Leu
            20                  25                  30

Ile Leu Pro Lys Ile Trp Asp Tyr Arg Asn Met Asn Thr Ala Leu Ile
        35                  40                  45

Lys Arg Asn Arg Tyr Thr Pro Glu Thr Gly Arg Lys Ser
    50                  55                  60

<210> SEQ ID NO 10
<211> LENGTH: 15
<212> TYPE: PRT
<213> ORGANISM: Homo sapiens

<400> SEQUENCE: 10

Met Glu Phe Ser Leu Leu Leu Pro Arg Leu Glu Cys Asn Gly Ala
 1               5                  10                  15

<210> SEQ ID NO 11
<211> LENGTH: 15
<212> TYPE: PRT
<213> ORGANISM: Homo sapiens

<400> SEQUENCE: 11
```

-continued

Gly Ala Ile Ser Ala His Arg Asn Leu Arg Leu Pro Gly Ser Ser
1               5                   10                  15

<210> SEQ ID NO 12
<211> LENGTH: 17
<212> TYPE: PRT
<213> ORGANISM: Homo sapiens

<400> SEQUENCE: 12

Asp Ser Pro Ala Ser Ala Ser Pro Val Ala Gly Ile Thr Gly Met Cys
1               5                   10                  15
Thr

<210> SEQ ID NO 13
<211> LENGTH: 16
<212> TYPE: PRT
<213> ORGANISM: Homo sapiens

<400> SEQUENCE: 13

Met Cys Thr His Ala Arg Leu Ile Leu Tyr Phe Phe Leu Val Glu Met
1               5                   10                  15

<210> SEQ ID NO 14
<211> LENGTH: 11
<212> TYPE: PRT
<213> ORGANISM: Homo sapiens

<400> SEQUENCE: 14

Tyr Phe Phe Leu Val Glu Met Glu Phe Leu His
1               5                   10

<210> SEQ ID NO 15
<211> LENGTH: 11
<212> TYPE: PRT
<213> ORGANISM: Homo sapiens

<400> SEQUENCE: 15

Val Gly Gln Ala Gly Leu Glu Leu Pro Thr Ser
1               5                   10

<210> SEQ ID NO 16
<211> LENGTH: 17
<212> TYPE: PRT
<213> ORGANISM: Homo sapiens

<400> SEQUENCE: 16

Asp Asp Pro Ser Val Ser Ala Ser Gln Ser Ala Arg Tyr Arg Thr Gly
1               5                   10                  15
His

<210> SEQ ID NO 17
<211> LENGTH: 14
<212> TYPE: PRT
<213> ORGANISM: Homo sapiens

<400> SEQUENCE: 17

Thr Gly His His Ala Arg Leu Cys Leu Ala Asn Phe Cys Gly
1               5                   10

<210> SEQ ID NO 18
<211> LENGTH: 17
<212> TYPE: PRT
<213> ORGANISM: Homo sapiens

```
<400> SEQUENCE: 18

Ala Asn Phe Cys Gly Arg Asn Arg Val Ser Leu Met Cys Pro Ser Trp
  1               5                  10                  15

Ser

<210> SEQ ID NO 19
<211> LENGTH: 19
<212> TYPE: PRT
<213> ORGANISM: Homo sapiens

<400> SEQUENCE: 19

Pro Glu Leu Lys Gln Ser Thr Cys Leu Ser Leu Pro Lys Cys Trp Asp
  1               5                  10                  15

Tyr Arg Arg

<210> SEQ ID NO 20
<211> LENGTH: 17
<212> TYPE: PRT
<213> ORGANISM: Homo sapiens

<400> SEQUENCE: 20

Leu Lys Gln Ser Thr Cys Leu Ser Leu Pro Lys Cys Trp Asp Tyr Arg
  1               5                  10                  15

Arg

<210> SEQ ID NO 21
<211> LENGTH: 14
<212> TYPE: PRT
<213> ORGANISM: Homo sapiens

<400> SEQUENCE: 21

Ser Thr Cys Leu Ser Leu Pro Lys Cys Trp Asp Tyr Arg Arg
  1               5                  10

<210> SEQ ID NO 22
<211> LENGTH: 11
<212> TYPE: PRT
<213> ORGANISM: Homo sapiens

<400> SEQUENCE: 22

Leu Ser Leu Pro Lys Cys Trp Asp Tyr Arg Arg
  1               5                  10

<210> SEQ ID NO 23
<211> LENGTH: 13
<212> TYPE: PRT
<213> ORGANISM: Homo sapiens

<400> SEQUENCE: 23

Lys Cys Trp Asp Tyr Arg Arg Ala Ala Val Pro Gly Leu
  1               5                  10

<210> SEQ ID NO 24
<211> LENGTH: 19
<212> TYPE: PRT
<213> ORGANISM: Homo sapiens

<400> SEQUENCE: 24

Lys Cys Trp Asp Tyr Arg Arg Ala Ala Val Pro Gly Leu Phe Ile Leu
  1               5                  10                  15

Phe Phe Leu
```

-continued

<210> SEQ ID NO 25
<211> LENGTH: 24
<212> TYPE: PRT
<213> ORGANISM: Homo sapiens

<400> SEQUENCE: 25

Lys Cys Trp Asp Tyr Arg Arg Ala Ala Val Pro Gly Leu Phe Ile Leu
 1               5                  10                  15

Phe Phe Leu Arg His Arg Cys Pro
            20

<210> SEQ ID NO 26
<211> LENGTH: 38
<212> TYPE: PRT
<213> ORGANISM: Homo sapiens

<400> SEQUENCE: 26

Lys Cys Trp Asp Tyr Arg Arg Ala Ala Val Pro Gly Leu Phe Ile Leu
 1               5                  10                  15

Phe Phe Leu Arg His Arg Cys Pro Thr Leu Thr Gln Asp Glu Val Gln
            20                  25                  30

Trp Cys Asp His Ser Ser
        35

<210> SEQ ID NO 27
<211> LENGTH: 5
<212> TYPE: PRT
<213> ORGANISM: Homo sapiens

<400> SEQUENCE: 27

Trp Asp Tyr Arg Arg
 1               5

<210> SEQ ID NO 28
<211> LENGTH: 13
<212> TYPE: PRT
<213> ORGANISM: Homo sapiens

<400> SEQUENCE: 28

Phe Ile Leu Phe Phe Leu Arg His Arg Cys Pro Thr Leu
 1               5                  10

<210> SEQ ID NO 29
<211> LENGTH: 25
<212> TYPE: PRT
<213> ORGANISM: Homo sapiens

<400> SEQUENCE: 29

Phe Ile Leu Phe Phe Leu Arg His Arg Cys Pro Thr Leu Thr Gln Asp
 1               5                  10                  15

Glu Val Gln Trp Cys Asp His Ser Ser
            20                  25

<210> SEQ ID NO 30
<211> LENGTH: 29
<212> TYPE: PRT
<213> ORGANISM: Homo sapiens

<400> SEQUENCE: 30

His Arg Cys Pro Thr Leu Thr Gln Asp Glu Val Gln Trp Cys Asp His
 1               5                  10                  15

Ser Ser Leu Gln Pro Ser Thr Pro Glu Ile Lys His Pro

-continued

```
                20                  25

<210> SEQ ID NO 31
<211> LENGTH: 14
<212> TYPE: PRT
<213> ORGANISM: Homo sapiens

<400> SEQUENCE: 31

Pro Ala Ser Ala Ser Gln Val Ala Gly Thr Lys Asp Met His
 1               5                  10

<210> SEQ ID NO 32
<211> LENGTH: 18
<212> TYPE: PRT
<213> ORGANISM: Homo sapiens

<400> SEQUENCE: 32

Asp Met His His Tyr Thr Trp Leu Ile Phe Ile Phe Ile Phe Asn Phe
 1               5                  10                  15

Leu Arg

<210> SEQ ID NO 33
<211> LENGTH: 19
<212> TYPE: PRT
<213> ORGANISM: Homo sapiens

<400> SEQUENCE: 33

His Tyr Thr Trp Leu Ile Phe Ile Phe Ile Phe Asn Phe Leu Arg Gln
 1               5                  10                  15

Ser Leu Asn

<210> SEQ ID NO 34
<211> LENGTH: 45
<212> TYPE: PRT
<213> ORGANISM: Homo sapiens

<400> SEQUENCE: 34

Ser Val Thr Gln Ala Gly Val Gln Trp Arg Asn Leu Gly Ser Leu Gln
 1               5                  10                  15

Pro Leu Pro Pro Gly Phe Lys Leu Phe Ser Cys Pro Ser Leu Leu Ser
                20                  25                  30

Ser Trp Asp Tyr Arg Arg Pro Arg Leu Ala Asn Phe
            35                  40                  45

<210> SEQ ID NO 35
<211> LENGTH: 19
<212> TYPE: PRT
<213> ORGANISM: Homo sapiens

<400> SEQUENCE: 35

Pro Gly Phe Lys Leu Phe Ser Cys Pro Ser Leu Leu Ser Ser Trp Asp
 1               5                  10                  15

Tyr Arg Arg

<210> SEQ ID NO 36
<211> LENGTH: 24
<212> TYPE: PRT
<213> ORGANISM: Homo sapiens

<400> SEQUENCE: 36

Phe Lys Leu Phe Ser Cys Pro Ser Leu Leu Ser Ser Trp Asp Tyr Arg
 1               5                  10                  15
```

Arg Pro Pro Arg Leu Ala Asn Phe
            20

<210> SEQ ID NO 37
<211> LENGTH: 14
<212> TYPE: PRT
<213> ORGANISM: Homo sapiens

<400> SEQUENCE: 37

Phe Ser Cys Pro Ser Leu Leu Ser Ser Trp Asp Tyr Arg Arg
 1               5                  10

<210> SEQ ID NO 38
<211> LENGTH: 10
<212> TYPE: PRT
<213> ORGANISM: Homo sapiens

<400> SEQUENCE: 38

Ser Leu Leu Ser Ser Trp Asp Tyr Arg Arg
 1               5                  10

<210> SEQ ID NO 39
<211> LENGTH: 5
<212> TYPE: PRT
<213> ORGANISM: Homo sapiens

<400> SEQUENCE: 39

Ser Ser Trp Asp Tyr
 1               5

<210> SEQ ID NO 40
<211> LENGTH: 7
<212> TYPE: PRT
<213> ORGANISM: Homo sapiens

<400> SEQUENCE: 40

Ser Ser Trp Asp Tyr Arg Arg
 1               5

<210> SEQ ID NO 41
<211> LENGTH: 25
<212> TYPE: PRT
<213> ORGANISM: Homo sapiens

<400> SEQUENCE: 41

Ser Ser Trp Asp Tyr Arg Arg Pro Pro Arg Leu Ala Asn Phe Phe Val
 1               5                  10                  15

Phe Leu Val Glu Met Gly Phe Thr Met
            20                  25

<210> SEQ ID NO 42
<211> LENGTH: 11
<212> TYPE: PRT
<213> ORGANISM: Homo sapiens

<400> SEQUENCE: 42

Phe Val Phe Leu Val Glu Met Gly Phe Thr Met
 1               5                  10

<210> SEQ ID NO 43
<211> LENGTH: 23
<212> TYPE: PRT
<213> ORGANISM: Homo sapiens -continued

```
<400> SEQUENCE: 43

Met Gly Phe Thr Met Phe Ala Arg Leu Ile Leu Ile Ser Gly Pro Cys
 1               5                  10                  15

Asp Leu Pro Ala Ser Ala Ser
             20

<210> SEQ ID NO 44
<211> LENGTH: 5
<212> TYPE: PRT
<213> ORGANISM: Homo sapiens

<400> SEQUENCE: 44

Ile Ser Gly Pro Cys
 1               5

<210> SEQ ID NO 45
<211> LENGTH: 17
<212> TYPE: PRT
<213> ORGANISM: Homo sapiens

<400> SEQUENCE: 45

Asp Leu Pro Ala Ser Ala Ser Gln Ser Ala Gly Ile Thr Gly Val Ser
 1               5                  10                  15

His

<210> SEQ ID NO 46
<211> LENGTH: 17
<212> TYPE: PRT
<213> ORGANISM: Homo sapiens

<400> SEQUENCE: 46

Gly Val Ser His His Ala Arg Leu Ile Phe Asn Phe Cys Leu Phe Glu
 1               5                  10                  15

Met

<210> SEQ ID NO 47
<211> LENGTH: 10
<212> TYPE: PRT
<213> ORGANISM: Homo sapiens

<400> SEQUENCE: 47

Asn Phe Cys Leu Phe Glu Met Glu Ser His
 1               5                  10

<210> SEQ ID NO 48
<211> LENGTH: 46
<212> TYPE: PRT
<213> ORGANISM: Homo sapiens

<400> SEQUENCE: 48

Ser Val Thr Gln Ala Gly Val Gln Trp Pro Asn Leu Gly Ser Leu Gln
 1               5                  10                  15

Pro Leu Pro Pro Gly Leu Lys Arg Phe Ser Cys Leu Ser Leu Pro Ser
             20                  25                  30

Ser Trp Asp Tyr Gly His Leu Pro Pro His Pro Ala Asn Phe
             35                  40                  45

<210> SEQ ID NO 49
<211> LENGTH: 19
<212> TYPE: PRT
<213> ORGANISM: Homo sapiens
```

-continued

```
<400> SEQUENCE: 49

Pro Pro Gly Leu Lys Arg Phe Ser Cys Leu Ser Leu Pro Ser Ser Trp
 1               5                  10                  15

Asp Tyr Gly

<210> SEQ ID NO 50
<211> LENGTH: 14
<212> TYPE: PRT
<213> ORGANISM: Homo sapiens

<400> SEQUENCE: 50

Phe Ser Cys Leu Ser Leu Pro Ser Ser Trp Asp Tyr Gly His
 1               5                  10

<210> SEQ ID NO 51
<211> LENGTH: 9
<212> TYPE: PRT
<213> ORGANISM: Homo sapiens

<400> SEQUENCE: 51

Leu Ser Leu Pro Ser Ser Trp Asp Tyr
 1               5

<210> SEQ ID NO 52
<211> LENGTH: 37
<212> TYPE: PRT
<213> ORGANISM: Homo sapiens

<400> SEQUENCE: 52

Ser Ser Trp Asp Tyr Gly His Leu Pro Pro His Pro Ala Asn Phe Cys
 1               5                  10                  15

Ile Phe Ile Arg Gly Gly Val Ser Pro Tyr Leu Ser Gly Trp Ser Gln
                20                  25                  30

Thr Pro Asp Leu Arg
            35

<210> SEQ ID NO 53
<211> LENGTH: 1442
<212> TYPE: DNA
<213> ORGANISM: Homo sapiens
<220> FEATURE:
<221> NAME/KEY: CDS
<222> LOCATION: (15)..(1139)

<400> SEQUENCE: 53
tttttttttt tgag atg gag ttt tcg ctc ttg ttg ccc agg ctg gag tgc         50
                Met Glu Phe Ser Leu Leu Leu Pro Arg Leu Glu Cys
                 1               5                  10 aat ggc gca atc tca gct cac cgc aac ctc cgc ctc ccg ggt tca agc         98
Asn Gly Ala Ile Ser Ala His Arg Asn Leu Arg Leu Pro Gly Ser Ser
         15                  20                  25 gat tct cct gcc tca gcc tcc cca gta gct ggg att aca ggc atg tgc        146
Asp Ser Pro Ala Ser Ala Ser Pro Val Ala Gly Ile Thr Gly Met Cys
     30                  35                  40 acc cac gct cgg cta att ttg tat ttt ttt tta gta gag atg gag ttt        194
Thr His Ala Arg Leu Ile Leu Tyr Phe Phe Leu Val Glu Met Glu Phe
 45                  50                  55                  60 ctc cat gtt ggt cag gct ggt ctc gaa ctc ccg acc tca gat gat ccc        242
Leu His Val Gly Gln Ala Gly Leu Glu Leu Pro Thr Ser Asp Asp Pro
                 65                  70                  75 tcc gtc tcg gcc tcc caa agt gct aga tac agg act ggc cac cat gcc        290
Ser Val Ser Ala Ser Gln Ser Ala Arg Tyr Arg Thr Gly His His Ala
```

-continued

```
                        80                  85                  90
cgg ctc tgc ctg gct aat ttt tgt ggt aga aac agg gtt tca ctg atg    338
Arg Leu Cys Leu Ala Asn Phe Cys Gly Arg Asn Arg Val Ser Leu Met
        95                  100                 105 tgc cca agc tgg tct cct gag ctc aag cag tcc acc tgc ctc agc ctc    386
Cys Pro Ser Trp Ser Pro Glu Leu Lys Gln Ser Thr Cys Leu Ser Leu
    110                 115                 120 cca aag tgc tgg gat tac agg cgt gca gcc gtg cct ggc ctt ttt att    434
Pro Lys Cys Trp Asp Tyr Arg Arg Ala Ala Val Pro Gly Leu Phe Ile
125                 130                 135                 140 tta ttt ttt tta aga cac agg tgt ccc act ctt acc cag gat gaa gtg    482
Leu Phe Phe Leu Arg His Arg Cys Pro Thr Leu Thr Gln Asp Glu Val
                145                 150                 155 cag tgg tgt gat cac agc tca ctg cag cct tca act cct gag atc aag    530
Gln Trp Cys Asp His Ser Ser Leu Gln Pro Ser Thr Pro Glu Ile Lys
            160                 165                 170 cat cct cct gcc tca gcc tcc caa gta gct ggg acc aaa gac atg cac    578
His Pro Pro Ala Ser Ala Ser Gln Val Ala Gly Thr Lys Asp Met His
        175                 180                 185 cac tac acc tgg cta att ttt att ttt att ttt aat ttt ttg aga cag    626
His Tyr Thr Trp Leu Ile Phe Ile Phe Ile Phe Asn Phe Leu Arg Gln
    190                 195                 200 agt ctc aac tct gtc acc cag gct gga gtg cag tgg cgc aat ctt ggc    674
Ser Leu Asn Ser Val Thr Gln Ala Gly Val Gln Trp Arg Asn Leu Gly
205                 210                 215                 220 tca ctg caa cct ctg cct ccc ggg ttc aag tta ttc tcc tgc ccc agc    722
Ser Leu Gln Pro Leu Pro Pro Gly Phe Lys Leu Phe Ser Cys Pro Ser
                225                 230                 235 ctc ctg agt agc tgg gac tac agg cgc cca cca cgc cta gct aat ttt    770
Leu Leu Ser Ser Trp Asp Tyr Arg Arg Pro Pro Arg Leu Ala Asn Phe
            240                 245                 250 ttt gta ttt tta gta gag atg ggg ttc acc atg ttc gcc agg ttg atc    818
Phe Val Phe Leu Val Glu Met Gly Phe Thr Met Phe Ala Arg Leu Ile
        255                 260                 265 ttg atc tct gga cct tgt gat ctg cct gcc tcg gcc tcc caa agt gct    866
Leu Ile Ser Gly Pro Cys Asp Leu Pro Ala Ser Ala Ser Gln Ser Ala
    270                 275                 280 ggg att aca ggc gtg agc cac cac gcc cgg ctt att ttt aat ttt tgt    914
Gly Ile Thr Gly Val Ser His His Ala Arg Leu Ile Phe Asn Phe Cys
285                 290                 295                 300 ttg ttt gaa atg gaa tct cac tct gtt acc cag gct gga gtg caa tgg    962
Leu Phe Glu Met Glu Ser His Ser Val Thr Gln Ala Gly Val Gln Trp
                305                 310                 315 cca aat ctc ggc tca ctg caa cct ctg cct ccc ggg ctc aag cga ttc   1010
Pro Asn Leu Gly Ser Leu Gln Pro Leu Pro Pro Gly Leu Lys Arg Phe
            320                 325                 330 tcc tgt ctc agc ctc cca agc agc tgg gat tac ggg cac ctg cca cca   1058
Ser Cys Leu Ser Leu Pro Ser Ser Trp Asp Tyr Gly His Leu Pro Pro
        335                 340                 345 cac ccc gct aat ttt tgt att ttc att aga ggc ggg gtt tca cca tat   1106
His Pro Ala Asn Phe Cys Ile Phe Ile Arg Gly Gly Val Ser Pro Tyr
    350                 355                 360 ttg tca ggc tgg tct caa act cct gac ctc agg tgacccacct gcctcagcct  1159
Leu Ser Gly Trp Ser Gln Thr Pro Asp Leu Arg
365                 370                 375 tccaaagtgc tgggattaca ggcgtgagcc acctcaccca gccggctaat ttagataaaa  1219
aaatatgtag caatgggggg tcttgctatg ttgcccaggc tggtctcaaa cttctggctt  1279
catgcaatcc ttccaaatga gccacaacac ccagccagtc acatttttta aacagttaca  1339
```

```
tctttatttt agtatactag aaagtaatac aataaacatg tcaaacctgc aaattcagta    1399
gtaacagagt tcttttataa cttttaaaca aagctttaga gca                     1442
```